US012350250B2

(12) United States Patent
Nagaraj et al.

(10) Patent No.: US 12,350,250 B2
(45) Date of Patent: Jul. 8, 2025

(54) AGGRELYTES FOR TREATING OCULAR CONDITIONS

(71) Applicant: The Regents of the University of Colorado, a Body Corporate, Denver, CO (US)

(72) Inventors: Ram H. Nagaraj, Aurora, CO (US); Rooban B. Nahomi, Aurora, CO (US); Sandip Nandi, Goa (IN)

(73) Assignee: The Regent of the University of Colorado, a Body Corporate, Denver, CO (US)

( * ) Notice: Subject to any disclaimer, the term of this patent is extended or adjusted under 35 U.S.C. 154(b) by 4 days.

(21) Appl. No.: 18/193,910

(22) Filed: Mar. 31, 2023

(65) Prior Publication Data

US 2024/0115538 A1     Apr. 11, 2024

Related U.S. Application Data

(60) Provisional application No. 63/326,800, filed on Apr. 1, 2022.

(51) Int. Cl.
*A61K 31/223*     (2006.01)
*A61K 31/265*     (2006.01)
*A61P 27/10*     (2006.01)

(52) U.S. Cl.
CPC .......... *A61K 31/223* (2013.01); *A61K 31/265* (2013.01); *A61P 27/10* (2018.01)

(58) Field of Classification Search
CPC ............................... A61K 31/223; A61P 27/10
USPC .......................................................... 514/513
See application file for complete search history.

(56) References Cited

FOREIGN PATENT DOCUMENTS

| CA | 3078680 A1 | 5/2019 | | |
|---|---|---|---|---|
| GB | 2094301 A | 9/1982 | | |
| WO | 89/04825 A1 | 6/1989 | | |
| WO | 2003077898 A1 | 9/2003 | | |
| WO | 2010102192 A2 | 9/2010 | | |
| WO | WO-2021092470 A1 * | 5/2021 | ............ | A61K 31/223 |
| WO | WO-2021151044 A1 * | 7/2021 | ............. | A61K 31/16 |

OTHER PUBLICATIONS

James Katz et al.; Presbyopia—A Review of Current Treatment Options and Emerging Therapies; May 24, 2021; Clinical Ophthalmology, vol. 15, pp. 2167-2168. (Year: 2021).*
Panja et al., Aggrelyte-2 promotes protein solubility and decreases lens stiffness through lysine acetylation and disulfide reduction: Implications for treating presbyopia, 2023, Aging Cell, vol. 22, e13797, p. 13 (Year: 2023).*
Giustarini et al., N-Acetylcysteine ethyl ester (NACET): a novel lipophilic cell-permeable cysteine derivative with an unusual pharmacokinetic feature and remarkable antioxidant potential, Biochemical Pharmacology, vol. 84, 2012, pp. 1522-1533 (Year: 2012).*
Allen, Natalie , et al., "Medical Management of Cataracts: Promising or Pointless?", N Z Med Stud J, (2020), 31:28-29.
Bisht, Anjali , et al., "Carrier-Free Self-Built Aspirin Nanorods as Anti-Aggregation Agents Towards Alpha-Crystallin-Derived Peptide Aggregates: Potential Implications in Non-Invasive Cataract Therapy", J. Mater. Chem. B, (2019), 7:6945-6954.
Blakytny, Robert , et al., "Prevention of Cataract in Diabetic Rats By Aspirin, Paracetamol (Acetaminophen) and Ibuprofen", Experimental Eye Research (1992), 54(4):509-518.
Cheng, Hung , "Aspirin and Cataract", British Journal of Ophthalmology (1992), 76:257-258.
Elwood, Peter , et al., "New uses for old drugs: Aspirin—the first miracle drug", The Pharmaceutical Journal (2001), online | URI: 20004121.
Haque, Syed Ehtaishamul, et al., "Effect of Aspirin and Celecoxib on Lens Glutathione and Soluble Protein Profile in Naphthalene-Induced Cataract in Wistar Rats", Journal of Pharmacy Research (2016), 10(5):270-274.
Harding, John J., "Can Cataract Be Prevented?", Eye (1999), 13:454-456.
Harding, John , et al., "Drugs, Including Alcohol, That Act as Risk Factors for Cataract, and Possible Protection Against Cataract By Aspirin-Like Analgesics and Cyclopenthiazide", Br J Ophthalmol. (1988), 72(11):809-814.
Hartwig, A. , "Thioglycolic Acid and its Salts", The MAK Collection for Occupational Health and Safety, "Thioglycolic Acid and its Salts," (2016), 1(2)800-837.
Heruye, S. H. , et al., "Current Trends in the Pharmacotherapy of Cataracts", Pharmaceuticals (Basel) (2020), 16;13(1):15.
Kyselova, Z. , et al., "Pharmacological Prevention of Diabetic Cataract", Journal of Diabetes and Its Complications (2004), 18:129-140.
Swamy, M. S. , et al., "Inhibition of Lens Crystallin Glycation and High Molecular Weight Aggregate Formation By Aspirin in Vitro and in Vivo", Invest Ophthalmol Vis Sci. (1989), 30(6):1120-6.
Van Heyningen , et al., "Do Aspirin-Like Analgesics Protect Against Cataract? A Case-Control Study", Lancet (1986),1(8490):1111-1113.
Grillo, et al., "Interaction of [gamma]—Glutamyltranspeptidase with Clofibryl-S-acyl-glutathione in Vitro and in Vivo in Rat," Chem. Res. Toxicol., 14(8): 1033-1040 (2001).
Aroyan, et al., "Development of Cysteine-Catalyzed Enantioselective Rauhut-Currier Reaction," J. Org. Chem., 75 (17): 5784-5796 (2010).

* cited by examiner

*Primary Examiner* — Jeffrey H Murray
*Assistant Examiner* — Rilla Marie Samsell
(74) *Attorney, Agent, or Firm* — Vincent L. Carcano; CAPUANO IP PLLC

(57) ABSTRACT

Methods of treating, preventing, delaying, or reversing presbyopia in a subject involve administering a pharmaceutically effective amount of an aggrelyte to the subject. The aggrelyte may be one or more of N,S-diacetyl-L-cysteine methyl ester, S-acetyl-N-(3,3,-dimethylbutanoyl)-L-cysteinate, or N-acetyl cysteine methyl ester. The aggrelyte may be administered topically.

14 Claims, 26 Drawing Sheets

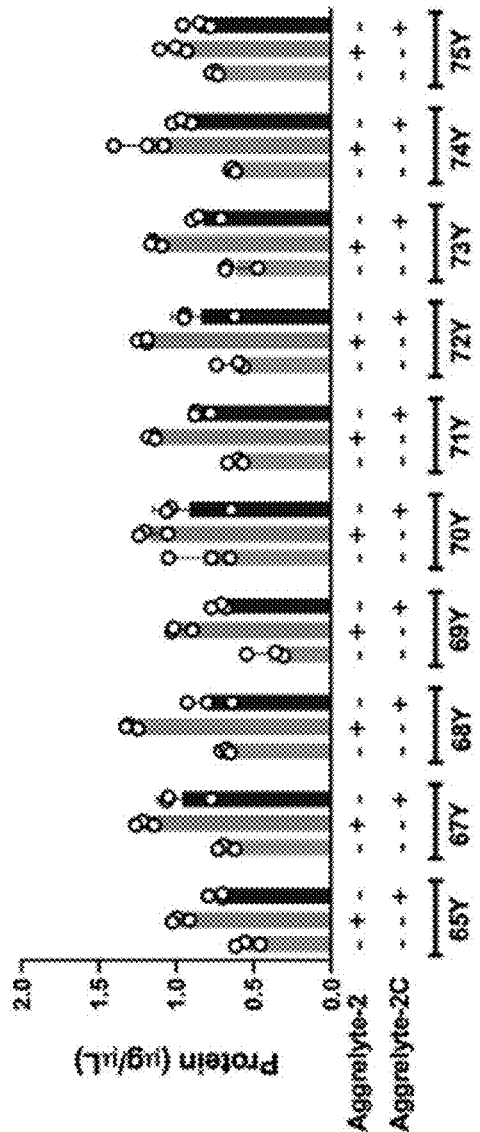
FIG. 5A
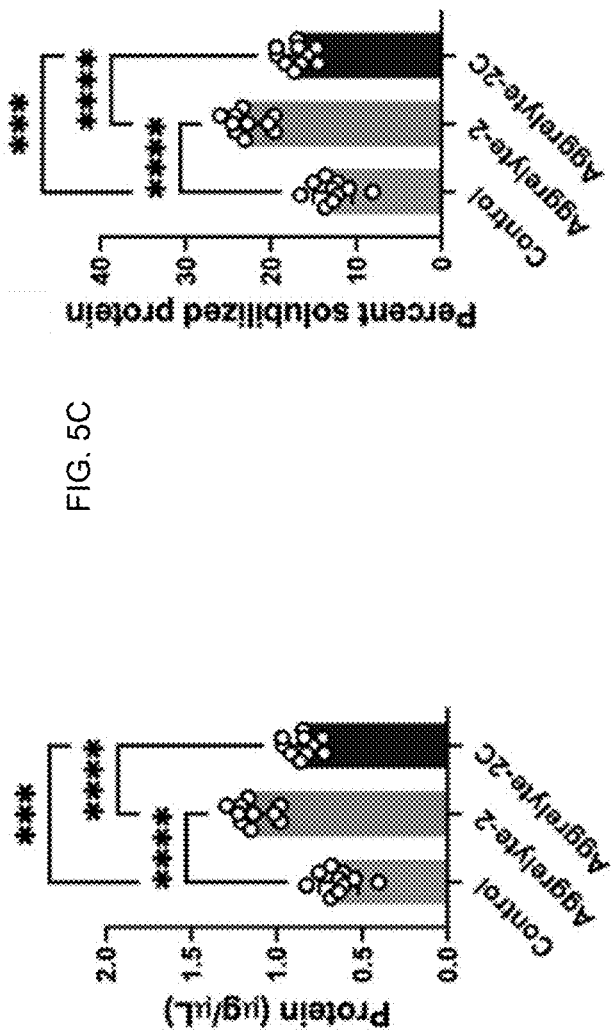
FIG. 5B
FIG. 5C

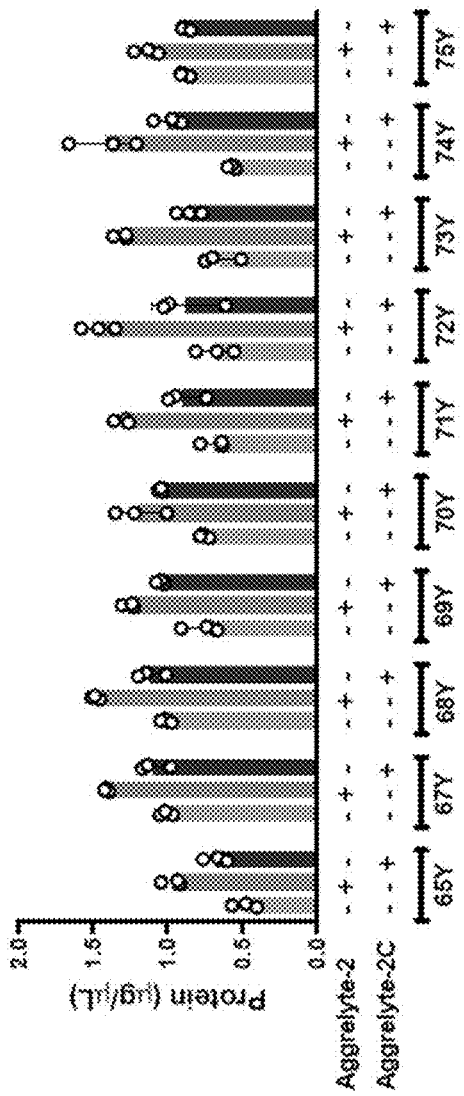
FIG. 5D
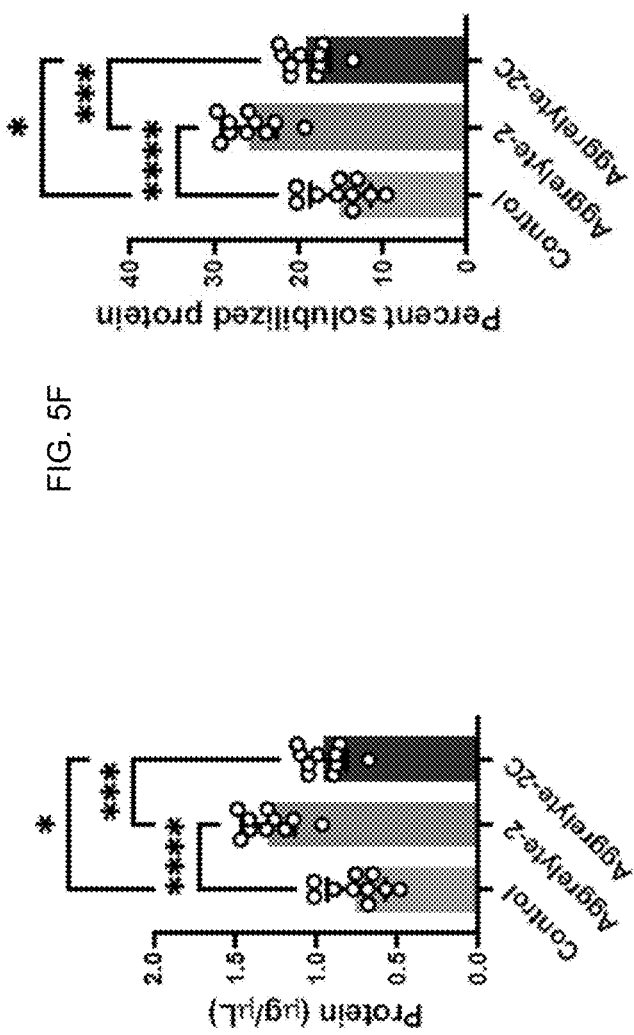
FIG. 5E
FIG. 5F

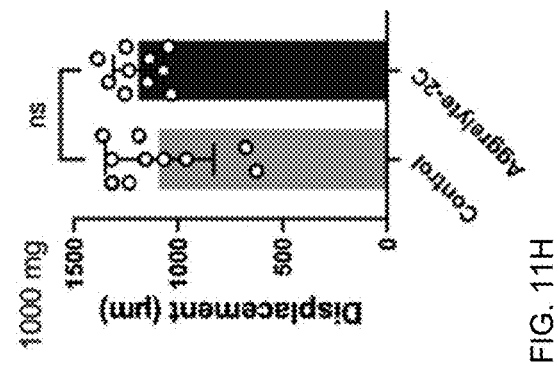
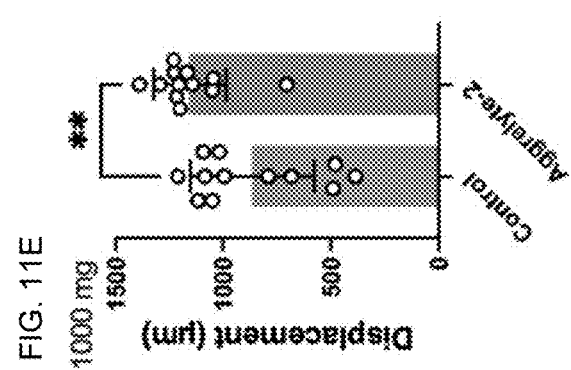
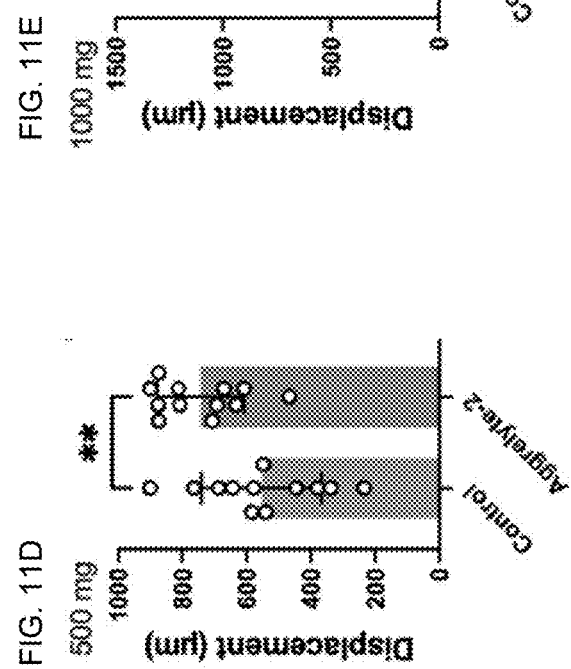
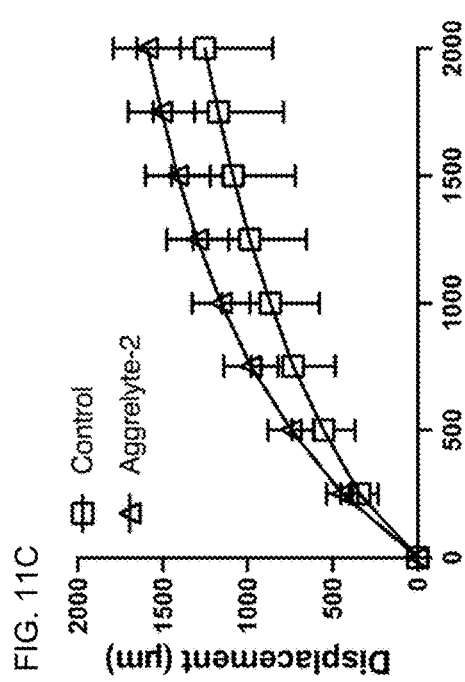
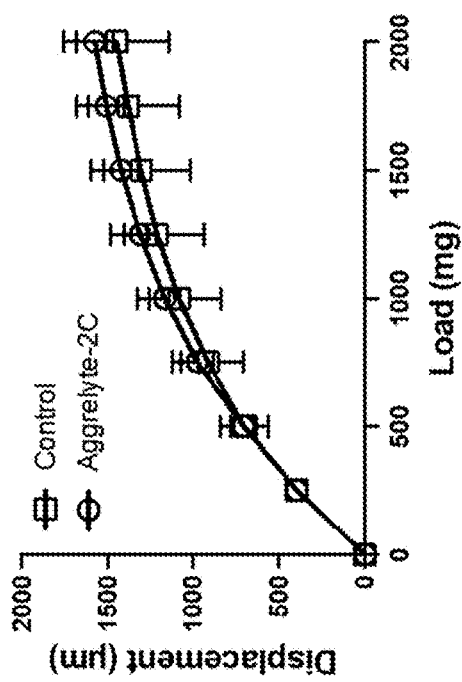
FIG. 11C  FIG. 11D  FIG. 11E
FIG. 11F  FIG. 11G  FIG. 11H

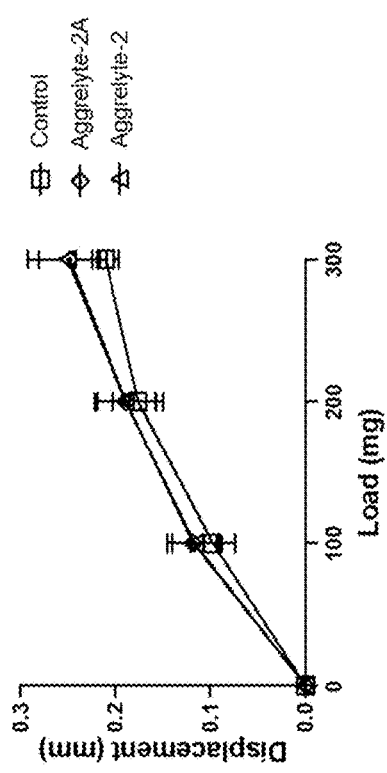
FIG. 18A
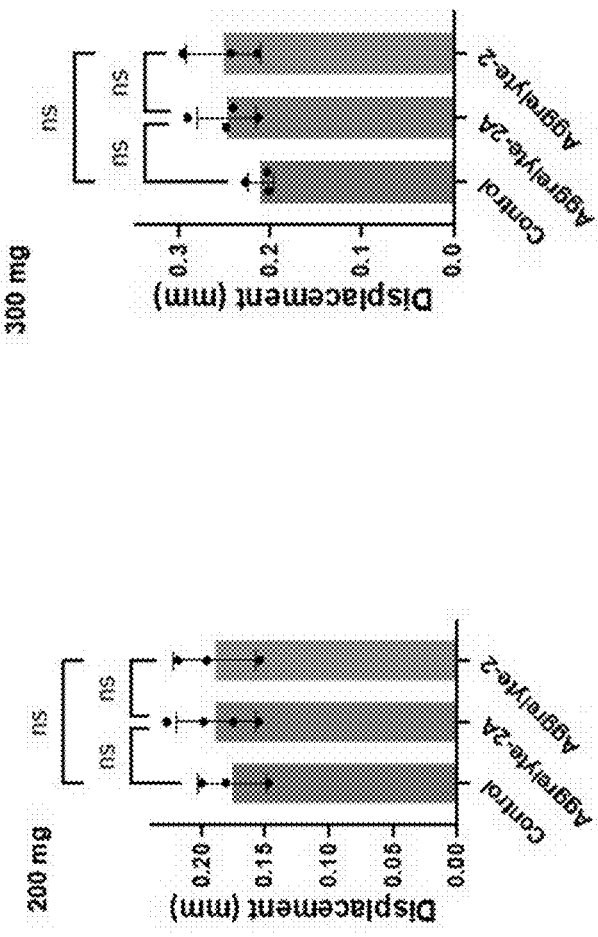
FIG. 18B
FIG. 18C

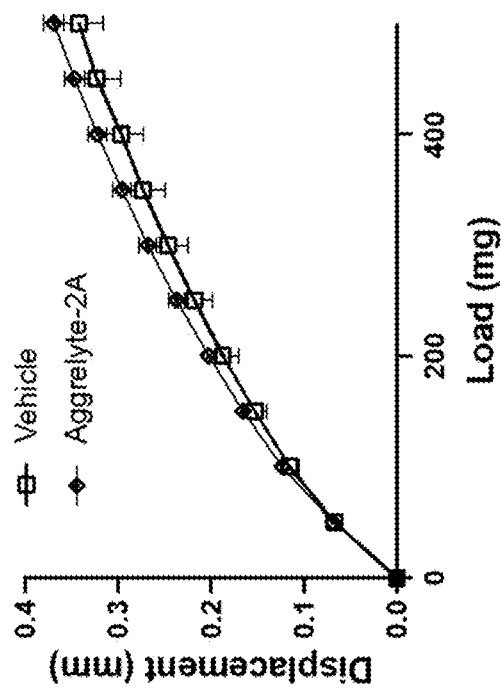
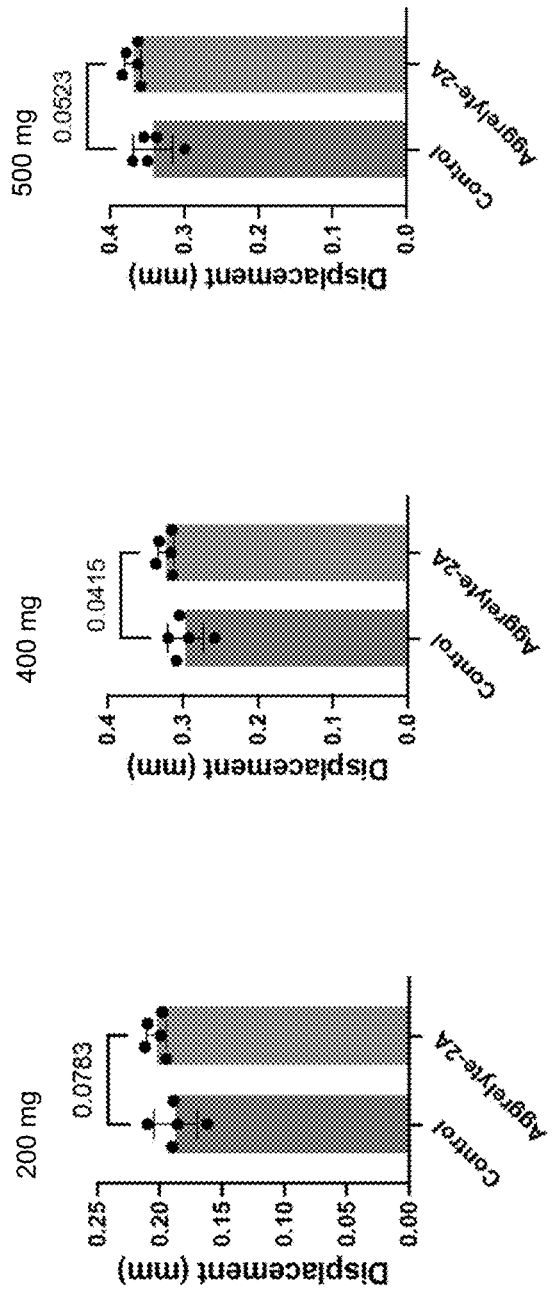
FIG. 21A
FIG. 21B
FIG. 21C
FIG. 21D

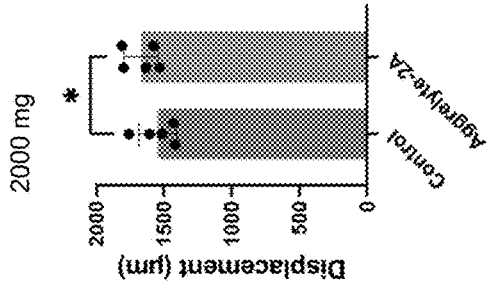
FIG. 25C
FIG. 25B
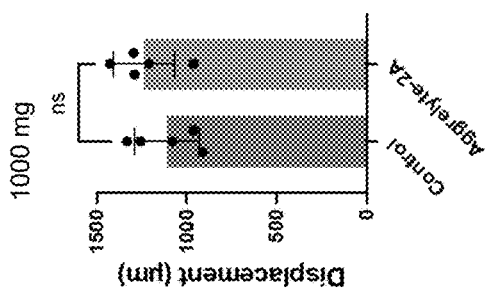
FIG. 25F
FIG. 25E
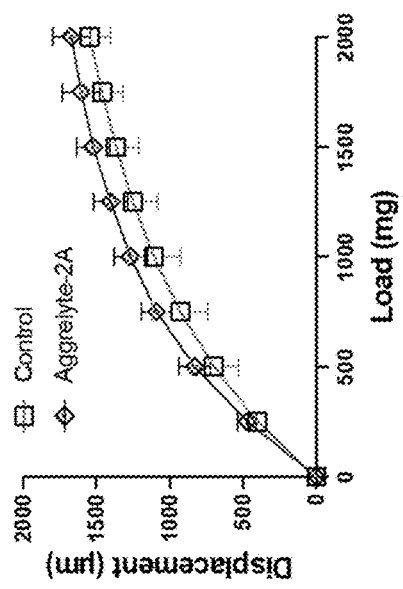
FIG. 25A
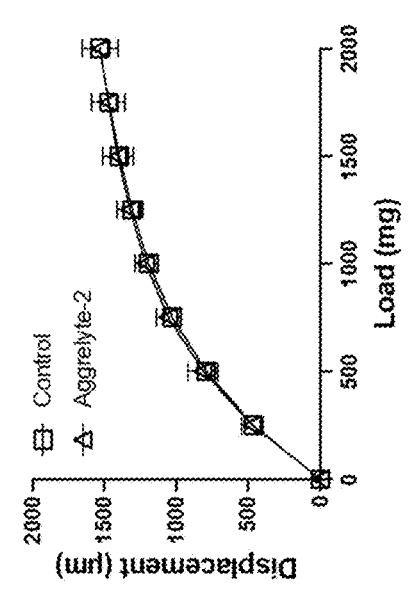
FIG. 25D

AGGRELYTES FOR TREATING OCULAR CONDITIONS

CROSS REFERENCE TO RELATED APPLICATION

The present application claims the benefit of priority under 35 U.S.C. § 119 to U.S. Provisional Patent Application No. 63/326,800, entitled "AGGRELYTES FOR TREATING OCULAR CONDITIONS," filed Apr. 1, 2022, the entirety of which is hereby incorporated by reference herein for all purposes.

STATEMENT OF GOVERNMENT INTEREST

This invention was made with government support from the National Institutes of Health and the National Eye Institute under grant numbers EY028836 and EY023286. The government has certain rights in the invention.

TECHNICAL FIELD

The present disclosure relates generally to compositions and methods for preventing, delaying, or reversing presbyopia. Specific implementations include administration of an aggrelyte to reduce lens stiffness.

BACKGROUND

Presbyopia is a major vision-impeding problem for many people over 40 years of age. As of 2015, an estimated 1.8 billion people globally were afflicted with presbyopia, nearly 26 million of which suffered visual impairment. In presbyopia, the lens loses the ability to accommodate. Age-associated hardening of the lens contributes to presbyopia. Lens proteins have little turnover and accumulate posttranslational modifications throughout life. Cumulative damage to lens proteins via posttranslational modifications leads to protein crosslinking, aggregation, insolubilization, and eventually lens stiffening. Accordingly, compositions and methods for treating, preventing, delaying, or reversing the onset of presbyopia are needed.

SUMMARY

Embodiments disclosed herein relate to compositions and methods for treating presbyopia by solubilizing aggregated lens proteins and/or decreasing lens stiffness (hardness) through one or more of acetylation of lens proteins and reduction of disulfide bonds in lens proteins.

In accordance with embodiments of the present disclosure, a method of treating, preventing, delaying, or reversing presbyopia in a subject may involve administering to the subject a therapeutically effective amount of a composition comprising at least one aggrelyte. In some examples, the aggrelyte is at least one of N,S-diacetyl-L-cysteine methyl ester, S-acetyl-N-(3,3-dimethylbutanoyl)-L-cysteinate, and N-acetyl cysteine methyl ester. In some examples, the aggrelyte composition is administered topically. In some examples, the aggrelyte composition is formulated as an ophthalmic drop, ophthalmic gel, or ophthalmic ointment. In some examples, the aggrelyte composition is administered intracamerally, intravitreally, or intravenously. In some embodiments, the aggrelyte composition is administered at least twice per day for four weeks. In some embodiments, the aggrelyte composition is administered to a human.

In accordance with embodiments of the present disclosure, a method of reducing eye lens stiffness may involve administering to the subject a therapeutically effective amount of a composition comprising at least one aggrelyte. In some examples, the aggrelyte is at least one of N,S-diacetyl-L-cysteine methyl ester, S-acetyl-N-(3,3-dimethylbutanoyl)-L-cysteinate, and N-acetyl cysteine methyl ester. In some examples, lens axial strain is reduced. In some examples, aggregated proteins in the lens are solubilized, and may be acetylated by the aggrelyte. In some examples, the eye lens is from a human, such as a lens that is at least 40 years old.

In accordance with embodiments of the present disclosure, a method of acetylating lysine residues in lens proteins may involve administering to the subject a therapeutically effective amount of a composition comprising at least one aggrelyte. In some examples, the aggrelyte is at least one of N,S-diacetyl-L-cysteine methyl ester, S-acetyl-N-(3,3-dimethylbutanoyl)-L-cysteinate, and N-acetyl cysteine methyl ester. In some examples, disulfide bonds of the lens proteins are broken. In some examples, lens proteins include human eye lens proteins, such as crystallins, which may be α-crystallin and βB2-crystallin.

This Summary is neither intended to be, nor should it be, construed as being representative of the full extent and scope of the present disclosure. Moreover, references made herein to "the present disclosure," or aspects thereof, should be understood to mean certain embodiments of the present disclosure and should not be construed as limiting all embodiments to a particular description. The present disclosure is set forth in various levels of detail in this Summary as well as in the attached drawings and Detailed Description and no limitation as to the scope of the present disclosure is intended by either the inclusion or non-inclusion of elements, components, etc. in this Summary. Features from any of the disclosed embodiments may be used in combination with one another without limitation. In addition, other features and advantages of the present disclosure will become apparent to those of ordinary skill in the art through consideration of the following Detailed Description and the accompanying drawings.

BRIEF DESCRIPTION OF THE DRAWINGS

The drawings illustrate several embodiments of the disclosure, wherein identical reference numerals refer to identical or similar elements or features in different views or embodiments shown in the drawings.

FIGS. 5A-5F are bar graphs showing the ability of Aggrelyte-2 and Aggrelyte-2C to solubilize human lens proteins after a 24-hour (FIGS. 5A-5C) or 48-hour (FIGS. 5D-5F) incubation.

FIGS. 11A-11E are graphs showing the effects of Aggrelyte-2 and Aggrelyte-2C on mouse and human lens stiffness. FIG. 11A is a line graph showing mouse lens displacement distance as a function of load mass. FIG. 11B is a bar graph showing mouse lens displacement distance for a 100-mg load. FIGS. 11C-11E show changes in displacement for human lenses treated with Aggrelyte-2 at loads of 500 mg (FIG. 11D) and 1000 mg (FIG. 11E). FIGS. 11F-11H show changes in displacement for human lenses treated with Aggrelyte-2C at loads of 500 mg (FIG. 11G) and 1000 mg (FIG. 11H).

FIG. 14B shows the cortical protein fraction and FIG. 14C shows the nuclear fraction from human lenses treated with Aggrelyte-2. FIG. 14D shows the cortical protein fraction and FIG. 14E shows the nuclear fraction from human lenses treated with Aggrelyte-2C.

FIG. 15B shows the cortical protein fraction and FIG. 15C shows the nuclear fraction from human lenses.

FIGS. 18A-18C are graphs showing the effects of Aggrelyte-2 and Aggrelyte-2A on mouse lens stiffness. FIG. 18A is a line graph showing lens displacement distance as a function of load mass. FIG. 18B is a bar graph showing displacement distance for a 200-mg load, and FIG. 18C is a bar graph showing displacement distance for a 300-mg load.

FIGS. 21A-21D are graphs showing the effects of topically applied Aggrelyte-2A on mouse lens stiffness. FIG. 21A is a line graph showing lens displacement distance as a function of load mass. FIGS. 21B-21D are bar graphs showing displacement distance for a 200-mg (21B), 400-mg (21C), or 500-mg (21D) load.

FIG. 24A shows anterior segment-optical coherence tomography (AS-OCT) images of corneas following vehicle or Aggrelyte-2A applications. FIG. 24B is a bar graph showing corneal thickness.

FIGS. 25A-25F are graphs showing the effects of Aggrelyte-2 and Aggrelyte-2A on human lens stiffness. FIGS. 25A and 25D are line graphs showing lens displacement distance as a function of load mass. FIGS. 25B and 25E are bar graphs showing displacement distance for a 1000-mg load; FIGS. 25C and 25F are bar graphs showing displacement distance for a 2000-mg load.

DETAILED DESCRIPTION

This disclosure relates to compositions and methods for treating, preventing, delaying, or reversing presbyopia. The methods disclosed herein involve solubilizing aggregated lens proteins and/or decreasing lens stiffness (hardness) via administration of an exogenous aggrelyte.

Figure 1B:
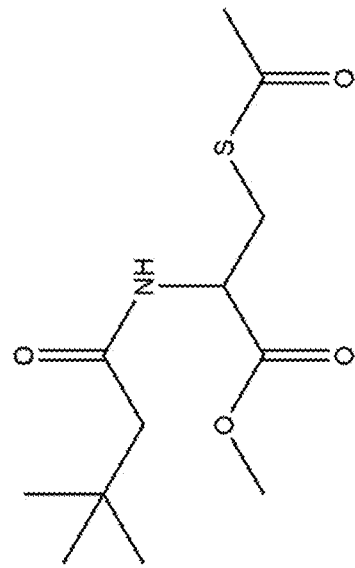
FIGS. 1A-1C show the structure of Aggrelyte-2 (FIG. 1A), Aggrelyte-2A (FIG. 1B), and Aggrelyte-2C (FIG. 1C).
Figure 1A:
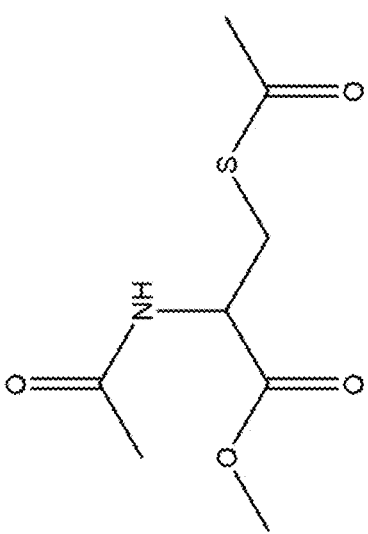
Figure 1C:
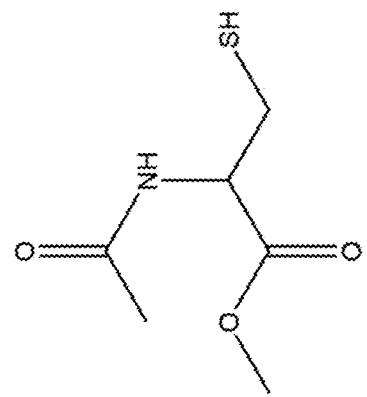

The aggrelyte may be selected from one or more of the compounds depicted in FIGS. 1A-1C, which may be called N,S-diacetyl-L-cysteine methyl ester ("Aggrelyte-2"), S-acetyl-N-(3,3,-dimethylbutanoyl)-L-cysteinate ("Aggrelyte-2A"), and N-acetyl-L-cysteine methyl ester ("Aggrelyte-2C"). Administration of an aggrelyte in the manner disclosed may cause acetylation of lens proteins and/or a breaking of disulfide bonds in lens proteins. The particular dose of aggrelyte may vary and may depend on the specific compound, the route of administration, and other factors.

As used herein, an "aggrelyte" is an acetylated cysteine derivative. Examples of aggrelytes are shown in FIGS. 1A-1C. Aggrelyte-2 has the structure shown in FIG. 1A. Under some naming conventions, Aggrelyte-2 is also known as N,S-diacetyl-L-cysteine methyl ester or methyl N,S-diacetyl cysteinate. Aggrelyte-2A has the structure shown in FIG. 1B. Under some naming conventions, Aggrelyte-2A is also known as methyl S-acetyl-N-(3,3,-dimethylbutanoyl)-L-cysteinate or methyl S-acetyl-N-(3,3-dimethylbutanoyl) cysteinate. Aggrelyte-2C has the structure shown in FIG. 1C. Under some naming conventions, Aggrelyte-2C is also known as N-acetyl cysteine methyl ester or methyl acetyl cysteinate.

Treating presbyopia, as contemplated herein, encompasses treating, preventing, delaying, or reversing at least one symptom of presbyopia. Accordingly, "treating" or "treatment" or "alleviation" refers to both therapeutic treatment and prophylactic or preventative measures, wherein the object is to prevent, postpone, or slow down (lessen) the targeted pathological condition, disorder and/or symptom. Those in need of treatment include those already with the condition as well as those prone to have the condition or those in whom the condition is to be prevented. A subject is successfully "treated" for presbyopia if, after receiving a therapeutic amount of an aggrelyte according to methods of this disclosure, the subject shows observable and/or measurable reduction in, or absence of, one or more of vision loss, lens stiffness, and lens protein insolubility. The terms "treat" or "treating" are used consistently herein for ease of illustration, only, and thus should not be construed as limiting.

An "effective amount" of an aggrelyte is an amount sufficient to carry out a specifically stated purpose. An "effective amount" may be determined empirically and in a routine manner, in relation to the stated purpose. The term "therapeutically effective amount" refers to an amount of an aggrelyte to "treat" presbyopia in a subject.

As used herein, "subject" means a human or other mammal. Non-human subjects may include, but are not limited to, various mammals including domestic pets and/or livestock. A subject can be considered in need of treatment. The disclosed methods and systems may be effective to treat healthy human subjects, patients diagnosed with presbyopia, or patients experiencing vision loss.

"Reducing," "reduce," or "reduction" means decreasing the severity, scope, or degree of presbyopia or a symptom or cause thereof.

"Administration of" and "administering a" compound, composition, or agent should be understood to mean providing a compound, composition, or agent; a prodrug of a compound, composition, or agent; or a pharmaceutical composition as described herein. The compound, composition, or agent can be provided or administered by another person to the subject (e.g., intracamerally, intravitreally, or intravenously) or it can be self-administered by the subject (e.g., as an eye drop or topical ointment). The compound, composition, or agent may be an aggrelyte.

"Pharmaceutical compositions" or "pharmaceutical formulations" are compositions that include an amount (for example, a unit dosage) of one or more of the disclosed aggrelytes together with one or more non-toxic pharmaceutically acceptable additives, including carriers, diluents, and/or adjuvants, and optionally other biologically active ingredients. Such pharmaceutical compositions can be prepared by standard pharmaceutical formulation techniques such as those disclosed in Remington's Pharmaceutical Sciences, Mack Publishing Co., Easton, Pa. (19th Edition).

As used herein, a "pharmaceutically acceptable excipient" or a "pharmaceutically acceptable carrier" means a pharmaceutically acceptable material, composition, or vehicle involved in giving form or consistency to the pharmaceutical composition. Each excipient or carrier should be compatible with other ingredients of the pharmaceutical composition when comingled such that interactions that would substantially reduce the efficacy of the aggrelyte formulations of this disclosure when administered to a subject and interactions that would result in pharmaceutical compositions that are not pharmaceutically acceptable are avoided. In addition, each excipient or carrier should be of sufficiently high purity to render it pharmaceutically acceptable.

Prodrugs of the disclosed aggrelytes, as active pharmaceutical ingredients, are also contemplated herein. A prodrug is an active or inactive compound that is modified chemically through in vivo physiological action, such as hydrolysis, metabolism, and the like, into an active agent following administration of the prodrug to a subject. The term "prodrug" as used throughout this disclosure means the pharmacologically acceptable derivatives such as esters, amides, and phosphates, such that the resulting in vivo biotransformation product of the derivative is an active pharmaceutical ingredient as described herein. Prodrugs may preferably have improved aqueous solubility and/or increased bioavailability compared to the active pharmaceutical ingredient, and may be readily metabolized into the active agents in vivo. Prodrugs of aggrelytes described herein may be prepared by modifying functional groups present in the aggrelytes in such a way that the modifications are cleaved, either by routine manipulation or in vivo, to the parent aggrelyte. The suitability and techniques involved in making and using prodrugs are well known by those skilled in the art. For a general discussion of prodrugs involving esters see Svensson and Tunek, Drug Metabolism Reviews 165 (1988) and Bundgaard, Design of Prodrugs, Elsevier (1985).

The singular terms "a," "an," and "the" include plural referents unless context clearly indicates otherwise. Similarly, the word "or" is intended to include "and" unless the context clearly indicates otherwise. The term "comprises" means "includes." Also, "comprising A or B" means including A or B, or A and B, unless the context clearly indicates otherwise. The term "about" intended to include values or amounts up to and including 10% greater than or less than the recited value or amount. It is to be further understood that all molecular weight or molecular mass values given for compounds are approximate, and are provided for description. Although methods and materials similar or equivalent to those described herein can be used in the practice or testing of this disclosure, suitable methods and materials are described below. In addition, the materials, methods, and examples are illustrative only and not intended to be limiting.

Unless otherwise defined, all technical and scientific terms used herein have the same meaning as commonly understood by one of ordinary skill in the art to which this disclosure belongs. In the case of conflict, the present specification, including definitions, will control. All publications, patent applications, patents, and other references mentioned herein are incorporated by reference. The references cited herein are not admitted to be prior art.

Therapeutic Methods

The formulations containing one or more aggrelytes described herein are suitable for treating, preventing, delaying, or reversing at least one symptom of an ophthalmologic condition. Ophthalmologic conditions are those that negatively affect one or both eyes of a subject. Ophthalmologic conditions targeted by the therapeutic methods disclosed herein may damage or degrade eye lenses specifically. An example ophthalmologic condition is presbyopia.

Administration of one or more aggrelytes may prevent the loss of or restore an eye lens' ability to accommodate. Without being limited to any mechanism or mode of action, aggrelytes may prevent or reverse age-related changes in the lens. Consistent with this theory, aggrelytes may solubilize aggregated or water-insoluble lens proteins (e.g., Examples 3, 4, 7, and 11) and/or reduce lens stiffness (e.g., Examples 10, 18, 20, 22). Aggrelytes may achieve either or both results by increasing acetylation of lysine residues in lens proteins (e.g., Examples 5, 6, 12, 13, 19, 20, and 23). In examples, Aggrelyte-2 and Aggrelyte-2A may donate an S-acetyl group to a lysine residue. In examples, Aggrelyte-2 and Aggrelyte-2C may donate an N-acetyl group to lysine residues. Acetylation may be of crystallins, cytoskeletal proteins, and/or other lens proteins. Examples of crystallins acetylated by aggrelytes, such as Aggrelyte-2, include α-crystallin and βB2-crystallin (e.g., Example 8).

Aggrelytes may solubilize aggregated lens proteins and/or reduce lens stiffness by increasing thiol content of lens proteins (e.g., Examples 9 and 20). The increased thiol content may be a result of reducing disulfide bonds in lens proteins. In examples, Aggrelyte-2C may act as a reducing agent to break a disulfide bonds via its free thiol group. In examples, Aggrelyte-2 and Aggrelyte-2A may act as a reducing agent to break disulfide bonds via a free thiol group after donation of the S-acetyl group to a lysine residue.

Aggrelytes may reduce lens axial strain (e.g., Example 10). Aggrelytes may inhibit advanced glycation end product (AGE) formation (e.g., Example 15).

Aggrelyte administration may not have a toxic or negative effect on lens epithelial cells (e.g., Example 17) or on corneas (e.g., Example 21). Aggrelyte administration may not decrease or otherwise change eye lens transparency (e.g., Example 20).

In some implementations, aggrelytes are administered to aged lenses. For example, the lenses may be of humans at least 40 years of age or older, such as about 40 years to about 80 years (e.g., Examples 3-11, 14, and 22), about 40 years to about 70 years, about 40 years to about 60 years, about 50 years to about 80 years, about 50 years to about 70 years, or about 65 years to about 75 years. Compared to lenses of humans less than 40 years of age, the aged lenses may exhibit at least one of more lens stiffness, less lens protein solubility, more lens protein aggregation, less lens protein acetylation, and more lens protein disulfide bonds.

The formulations of this disclosure can be administered to a subject before or after onset of presbyopia. The frequency and duration of aggrelyte administration may vary. In embodiments, an effective amount of aggrelyte may be administered once a day for one or two days. In embodiments, an effective amount of aggrelyte may be administered twice daily for a four-week treatment period. Doses may be administered more than once or twice a day, such as three to six times per day. Doses may be administered on a weekly basis, for example one, two, three, four, five, six, or more times per week. Monthly administrations may also be implemented, such that aggrelyte acid formulations are administered one, two, three, four, or more times per month.

The number of times per day, week, or month that the disclosed formulations are administered to a subject, along with the entire duration of the treatment period, may depend on the severity or type of condition a subject is experiencing or is expected to experience. For example, embodiments in which an aggrelyte is administered to treat existing presbyopia may involve more frequent administrations than embodiments in which an aggrelyte is administered to prevent or delay the onset of presbyopia. Embodiments in which an aggrelyte is administered to prevent the onset of presbyopia may involve a longer treatment period than embodiments in which an aggrelyte is administered to treat existing presbyopia. For example, as a prophylactic, administration of aggrelyte formulations may commence when a subject is less than about 40 years old, such as about 35 years old, about 30 years old, or younger, and may continue for at least one year, such as about five years, about 10 years, or longer. The length of the treatment period may also be patient-specific and re-evaluated periodically by an ophthalmologist or other health care provider.

Pharmaceutical Formulations

Aggrelytes of this disclosure may be administered as a pharmaceutical formulation. Aggrelytes of this disclosure may be formulated into a pharmaceutical dosage form adapted for topical administration to a subject. Intracameral, intravitreal, intravenous, intra-arterial, subcutaneous, or intraperitoneal injection may also be used. Injection by such routes may use an injection device, such as an IV drip device, infusion pump, and/or tuberculin syringe.

In embodiments, the aggrelyte may be administered concurrently with one or more excipients. Suitable excipients may vary depending upon the particular dosage form chosen. In addition, suitable pharmaceutically acceptable excipients may be chosen for a particular function that they may serve in the formulation. Alternatively or additionally, certain pharmaceutically acceptable excipients may be chosen for their ability to facilitate the production of stable dosage forms, enhance bioavailability, and/or minimize side effects.

Excipients that may be used include buffering agents, carriers, diluents, fillers, binders, disintegrants, lubricants, glidants, granulating agents, coating agents, wetting agents, solvents, co-solvents, suspending agents, emulsifiers, coloring agents, anticaking agents, humectants, chelating agents, plasticizers, viscosity agents, antioxidants, preservatives, stabilizers, and surfactants. The skilled artisan will appreciate that certain pharmaceutically acceptable excipients may serve more than one function and may serve alternative functions depending on how much of the excipient is present in the formulation and what other ingredients are present in the formulation.

Aggrelytes may be provided as a topical ophthalmologic composition, such as a liquid (e.g., eye drop), gel, or ointment. Eye drops may be formulated with an aqueous or non-aqueous base also comprising one or more dispersing agents, solubilizing agents, or suspending agents.

Drops may be delivered by an eye dropper-capped bottle or by a plastic bottle adapted to deliver liquid contents dropwise by means of a specially shaped closure. Specific examples of suitable excipients for topical administration include surfactants such as benzalkonium chloride, buffers such as sodium dihydrogen phosphate monohydrate and disodium hydrogen phosphate, and carriers such as hypromellose. In one example, a topical composition includes at least one aggrelyte and a liquid formulation including benzalkonium chloride (0.001 wt %), sodium dihydrogen phosphate monohydrate (0.269 wt %), disodium hydrogen phosphate (0.433 wt %), hypromellose (0.2 wt %), and sodium chloride (0.5 wt %).

The therapeutically effective concentration or dosage of aggrelyte administered to a subject may vary depending on, for example, the nature of the formulation, mode of administration, particular condition to be treated, and condition and mass of the patient. Dosage levels are typically sufficient to achieve a tissue concentration at the site of action that is at least comparable to a concentration that has been shown to be active in vitro, in vivo, ex vivo, or in tissue culture. In an example, an aggrelyte is provided in a liquid formulation for topical administration at a concentration of about 40 mM to about 100 mM, or about 40 mM to about 80 mM, about 40 mM to about 60 mM, about 60 mM to about 100 mM, or about 80 mM to about 100 mM.

EXAMPLES

The following examples illustrate various aspects of the disclosure, and should not be considered limiting.

Example 1: Stability of Aggrelyte-2 and Aggrelyte-2C Under Physiological Conditions Aggrelyte-2 (N,S-diacetyl-L-cysteine methyl ester; Astatech Catalog #D95910) and Aggrelyte-2C (N-acetyl cysteine methyl ester; Sigma Aldrich Catalog #01042) (2 mg each) were incubated in 1 mL of 50 mM phosphate buffer, pH 7.4, at 37° C. Aliquots were withdrawn immediately after incubation (Day 0) and after 1, 3, and 7 days. Stability of the aggrelytes was tested using $^1$H-NMR (in DMSO-$d_6$) spectroscopy. The NMR peak integration values for the S-acetyl or N-acetyl cysteine methyl proton were compared with the cysteine methine proton.

Figure 2:
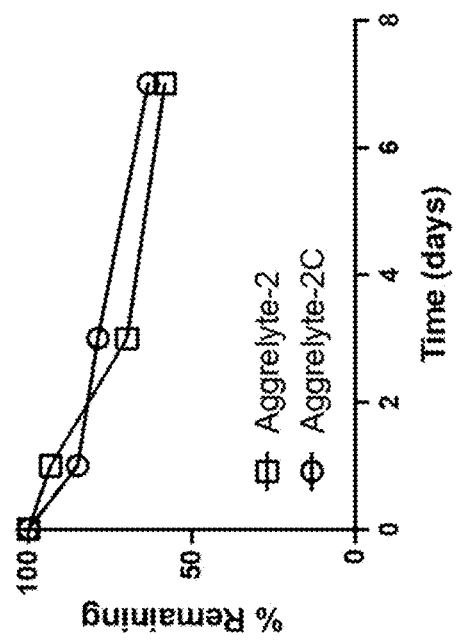
FIG. 2 is a line graph showing the stability of Aggrelyte-2 and Aggrelyte-2C under physiological conditions over seven days.

Results compiled from NMR spectral data are shown in FIG. 2. The aggrelytes were relatively stable for 24 hours but degraded by 30% and 42% (Aggrelyte-2) and 21% and 37% (Aggrelyte-2C) during the 3- and 7-day incubation periods, respectively.

Example 2: Relative Protein Acetylation Capability of Aggrelyte-2

The relative ability of Aggrelyte-2 to acetylate lysine residues in proteins was investigated using αA-crystallin (αAC). Human recombinant αAC (3 mg/mL PBS) was incubated in 50 mM sodium phosphate buffer, pH 7.4, for 24 hours at 37° C. while shaking without or with 500 μM acetylating agent (Aggrelyte-2, acetyl-CoA, acetic anhydride, or aspirin), dialyzed against PBS for 24 hours at 4° C.

Figure 3:
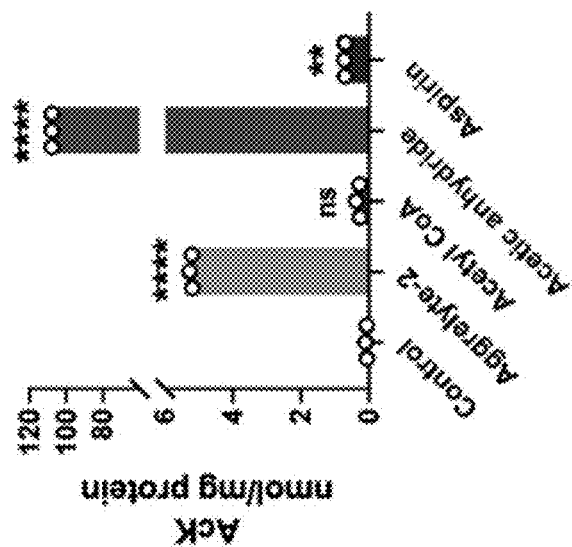
FIG. 3 is a bar graph showing a comparison of the acetylating ability of Aggrelyte-2 and other acetylating agents.

Results are shown in FIG. 3. Acetic anhydride was the most potent acetylating agent (~21-fold higher than Aggrelyte-2), followed by Aggrelyte-2, aspirin, and acetyl-CoA. =$p<0.01$, *=$p<0.001$, ****=$p<0.0001$, and ns=not significant, each as compared to Control.

Example 3: Ability of Aggrelyte-2 and Aggrelyte-2C to Solubilize Proteins from Human Lenses Human lenses (donor age: 55-75 years) were obtained from Saving Sight, Kansas City, MO, and Lions Eye Institute for Transplant & Research, Tampa, FL. The lenses were harvested within 36 hours postmortem, stored with (when used for culturing) or without minimum essential medium (MEM), and shipped to the inventors' laboratory on ice or frozen on dry ice. Lenses shipped on dry ice (used in the presently described and other solubility studies) were stored at −80° C. until use. Each frozen lens was thawed on ice and homogenized with 1.5 mL of PBS in a hand-held glass homogenizer. The homogenate was centrifuged at 20,000×g for 20 min at 4° C. The supernatant was discarded, and the pellet was suspended in 1 mL of homogenization buffer and centrifuged at 20,000×g for 20 min at 4° C. The resulting pellet was lyophilized and designated the water-insoluble (WI) fraction.

In the present example, the ability of aggrelytes to solubilize WI proteins from a 71-year-old human lens was investigated. Stock solutions (10 mM) of Aggrelyte-2 and Aggrelyte-2C were prepared in 50 mM phosphate buffer. The WI fraction (2 mg) was incubated in 50 mM sodium phosphate buffer (0.4 mL), pH 7.4, at 37° C. with aggrelyte at a final concentration of 0-2000 μM. The mixture was incubated at 37° C. with shaking for 24 or 48 hours after adding 0.002% sodium azide to prevent bacterial growth. After incubation, the samples were centrifuged at 20,000×g for 20 min at 4° C., and the supernatants were collected. Protein in the supernatant was measured using a BCA Protein Assay Kit from Thermo Scientific (Waltham, MA) using BSA as the standard.

Figure 4A:
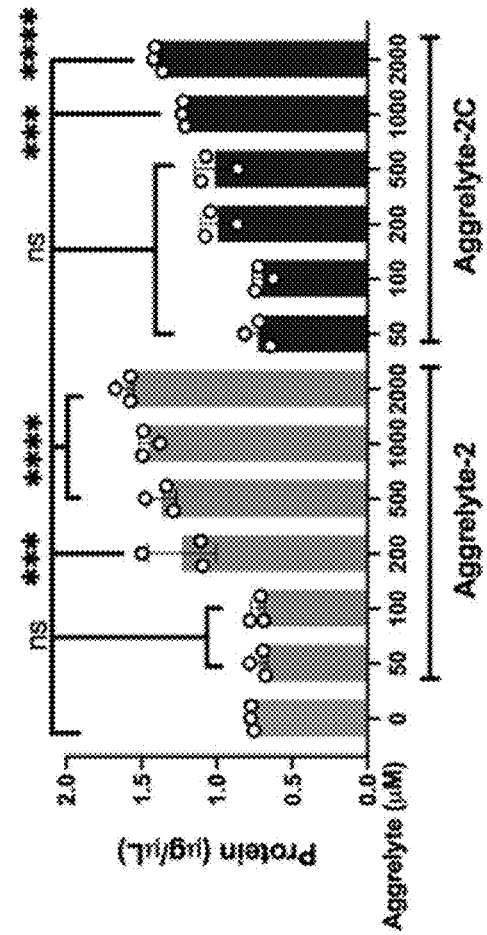
FIGS. 4A and 4B are bar graphs showing the ability of Aggrelyte-2 and Aggrelyte-2C to solubilize human lens proteins after a 24-hour (FIG. 4A) or 48-hour (FIG. 4B) incubation.
Figure 4B:
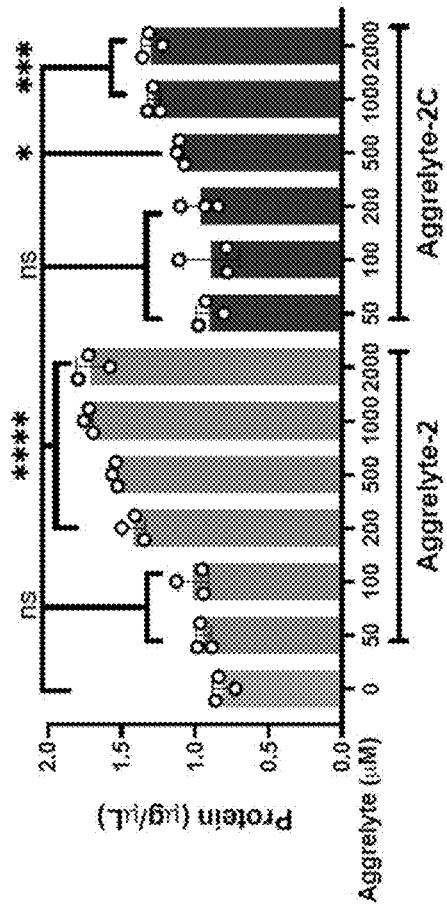

Results are shown in FIG. 4A (24 hours) and FIG. 4B (48 hours). Increasing concentrations of aggrelyte progressively increased the solubility of WI proteins. Aggrelyte-2 performed better than Aggrelyte-2C. At 500 μM and 48 hours, the protein solubility driven by Aggrelyte-2C was ~1.4-fold less than that of Aggrelyte-2. *=$p<0.05$, *=$p<0.001$, **=$p<0.0001$, and ns=not significant. Aggrelyte-2 and Aggrelyte-2C were used at 500 μM in the following Examples 4-15 unless otherwise noted.

Example 4: Ability of Aggrelyte-2 and Aggrelyte-2C to Solubilize Proteins from Human Lenses WI fractions from ten aged human lenses (65 to 75 years) were prepared as in Example 3. The WI fractions (2 mg) were incubated in 50 mM sodium phosphate buffer (0.4 mL), pH 7.4, at 37° C. with 500 μM aggrelyte for 24 or 48 hours. Each sample was separately processed three times and analyzed (mean±S.D.).

Results from the 24-hour treatment are presented in FIGS. 5A-5C. Each of the 10 tested lenses is shown in FIG. 5A. The combined effects (from the 10 lenses) of the aggrelytes on the solubilizaton of WI protein are shown in FIG. 5B. The percent solubilized protein from the initial weight of WI protein after a 24-hour treatment is shown in FIG. 5C. After a 24-hour incubation, control samples yielded 0.40-0.83 μg protein/μL in the supernatant (FIGS. 5A and 5B), which corresponds to 8-17% of the initial WI fraction (FIG. 5C). Upon incubation with Aggrelyte-2, the yield increased to 0.97-1.30 μg/μL in the supernatants (FIGS. 5A and 5B), reaching 20-26% of the initial WI protein (FIG. 5C). Under similar conditions, Aggrelyte-2C yielded 0.72-0.97 μg/μL protein (FIGS. 5A and 5B), corresponding to 14-19% of the initial WI fraction (FIG. 5C). *=$p<0.001$ and **=$p<0.0001$.

Results from the 48-hour treatment are presented in FIGS. 5D-5F. Each of the 10 tested lenses is shown in FIG. 5D. The combined effects (from the 10 lenses) of the aggrelytes on the solubilization of WI protein are shown in FIG. 5E. The percent solubilized protein from the initial weight of WI protein after a 24-hour treatment is shown in FIG. 5F. After a 48-hour incubation, control samples yielded 0.48-1.01 μg protein/μL in the supernatant (FIGS. 5D and 5E), which corresponds to 10-20% of the initial WI fraction (FIG. 5F). The incubation with Aggrelyte-2 and Aggrelyte-2C yielded 0.96-1.48 μg/μL and 0.68-1.12 μg/μL protein in the supernatants (FIGS. 5D and 5E), corresponding to 19-30% and 14-22% of the initial protein (FIG. 5F), respectively. *=$p<0.05$, *=$p<0.001$, and **=$p<0.0001$.

Collectively, the data demonstrate that Aggrelyte-2 was significantly ($p<0.001$) better (i.e., by ~1.4-fold) than Control or Aggrelyte-2C in solubilizing WI proteins in the samples incubated for 24 and 48 hours (FIGS. 5B and 5E). The soluble protein yield increased slightly in the samples incubated for 48 hours compared to those incubated for 24 hours. The ability of an aggrelyte to solubilize aggregated lens proteins may help decrease stiffness of aged lenses.

Example 5: Effects of Aggrelyte-2 and Aggrelyte-2C on Levels of Acetylated Proteins in Human Lenses (Western Blot Analysis)

The content of acetyllysine (AcK)-bearing proteins in the solubilized proteins from Examples 3 and 4 was determined by Western blot analysis. Proteins were separated on a 12% denaturing gel, transferred to a nitrocellulose membrane, blocked with 5% nonfat dry milk, and incubated with an antibody against N-acetyllysine (AcK antibody @ 1:5,000 dilution; Cell Signaling Technology, Catalog #9681S) for 16 hours, followed by incubation with horseradish peroxidase (HRP)-conjugated goat anti-mouse IgG (1:5,000 dilution; Cell Signaling Technology, Catalog #7076S) for 1 hour. Chemiluminescence was detected using an Enhanced Chemiluminescence Detection Kit (Thermo Scientific). Then the membrane was stained with Ponceau-S to visualize the proteins and normalize the detected AcK-bearing protein to the total protein load via densitometry.

Figure 6B:
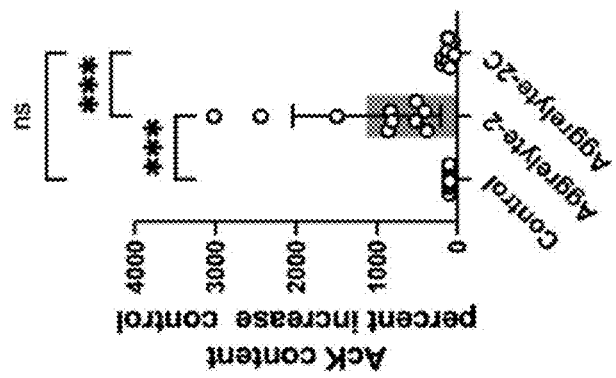
FIGS. 6A and 6B are bar graphs showing the effects of Aggrelyte-2 and Aggrelyte-2C on acetylation of human lens proteins generated from Western blot densitometric analysis.
Figure 6A:
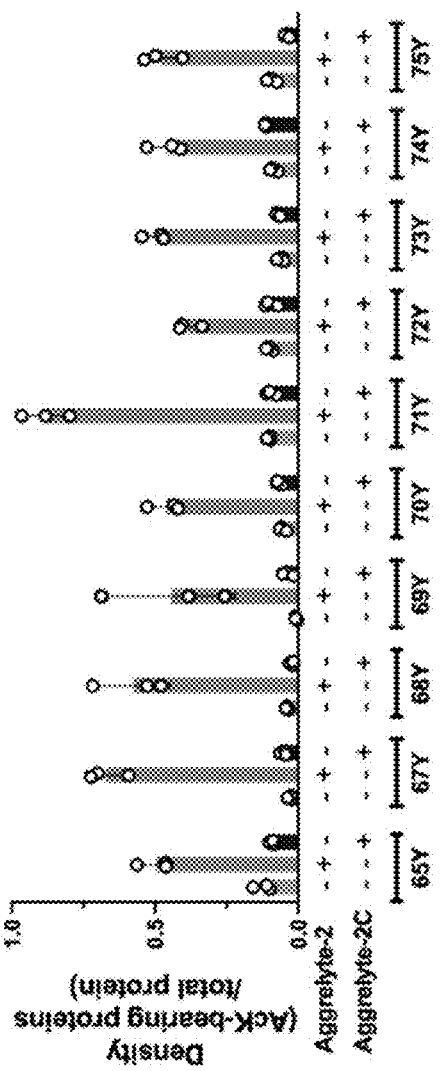

Results are shown in FIGS. 6A and 6B for the ten aged human lenses (65 to 75 years) of Example 4. The densitometric plot from the Western blot analysis (FIG. 6A) shows that incubation with Aggrelyte-2 significantly (p<0.001) increased the amount of AcK-bearing proteins compared to Control or Aggrelyte-2C, which did not increase the AcK levels.

The combined effects (from the 10 lenses) of the aggrelytes on AcK content is shown in FIG. 6B as percent increase in the AcK component of the solubilized protein content compared to Control (no aggrelyte) (mean±S.D.). *=p<0.001, **=p<0.0001, and ns=not significant.

The ability of an aggrelyte to acetylate lens proteins may help solubilize aggregated lens proteins and decrease lens stiffness.

Example 6: Effects of Aggrelyte-2 and Aggrelyte-2C on Levels of Acetylated Proteins in Human Lenses (LC-MS/MS Analysis)

Water-insoluble proteins were prepared from aged human lenses (55-67 years) as described in Example 3, and incubated with 0 or 500 µM Aggrelyte-2 or Aggrelyte-2C for 24 hours as described in Example 3. Solubilized WI protein fractions (0.5 mg/mL) and water soluble (WS) protein fractions (3 mg/mL from human lenses) were sequentially digested with enzymes as previously described (Nandi et al., 2019, Biochemistry, 58(9):1260-1274). The enzyme-digested samples were analyzed for AcK by LC-MS/MS using the standard addition method as previously described (id.) The AcK levels were calculated based on the protein input in the enzymatic digestions.

Figure 7B:
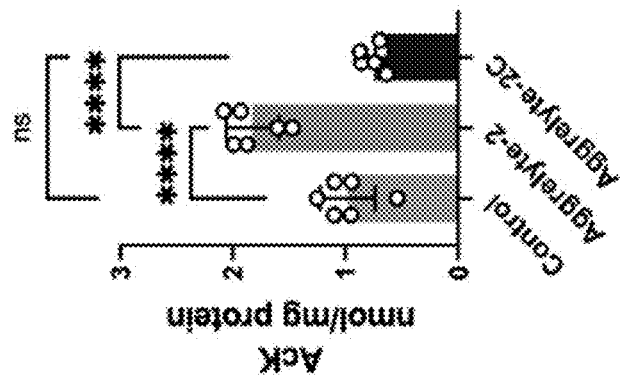
FIGS. 7A and 7B are bar graphs showing the effects of Aggrelyte-2 and Aggrelyte-2C on acetylation of human lens proteins generated from LC-MS/MS analysis.
Figure 7A:
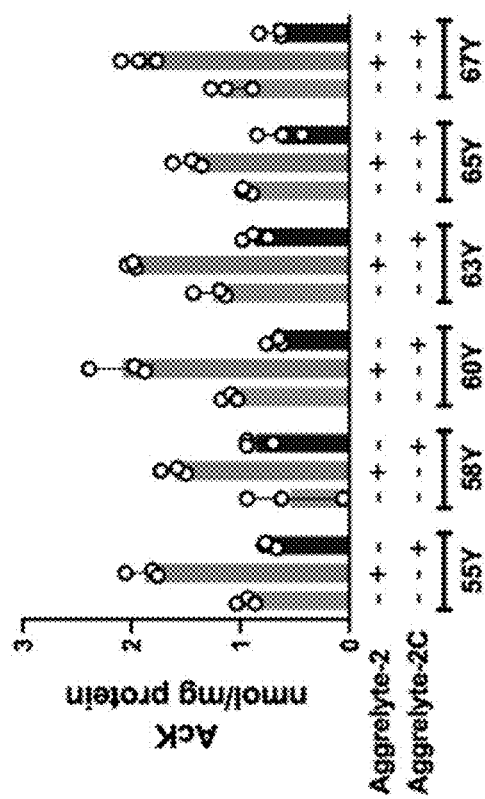

Results are presented in FIGS. 7A and 7B. Each sample was separately processed three times and analyzed, and the bar graphs represent the mean±S.D. LC-MS/MS analyses of the solubilized protein samples revealed 0.5-1.3 nmol of AcK/mg protein in the controls (FIG. 7A). Samples treated with Aggrelyte-2 contained 1.5-2.1 nmol/mg protein. The AcK levels in the Aggrelyte-2C-treated samples were comparable to those in the untreated controls (0.6-0.9 nmol/mg protein).

A combined plot of the mean values of the three analyses of each sample is shown in FIG. 7B. The AcK levels in the Aggrelyte-2-treated samples showed a significant (p<0.0001) 1.9- and 2.4-fold increase compared to the untreated controls and Aggrelyte-2C-treated samples, respectively. ****=p<0.0001 and ns=not significant.

The ability of an aggrelyte to acetylate lens proteins may help solubilize aggregated lens proteins and decrease lens stiffness.

Example 7: Relationship Between Protein Acetylation and Solubility

To determine whether protein acetylation alone contributed to lens protein solubility, the soluble protein levels in WI proteins treated with acetic anhydride and Aggrelyte-2 were compared.

Figure 8B:
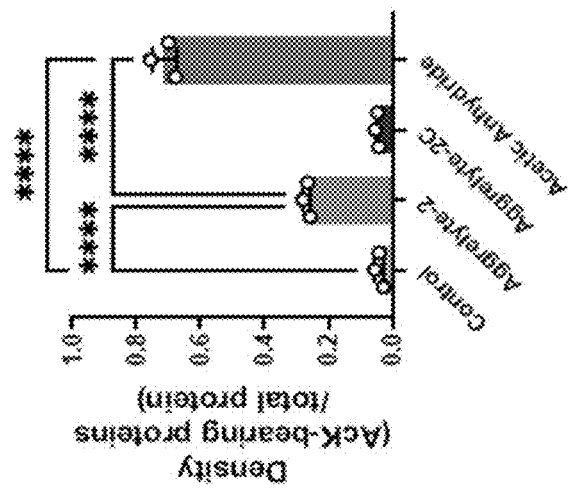
FIGS. 8A and 8B are bar graphs showing the ability of Aggrelyte-2 and Aggrelyte-2C to solubilize (FIG. 8A) and acetylate (FIG. 8B) human lens proteins compared to an acetylating agent, acetic anhydride.
Figure 8A:
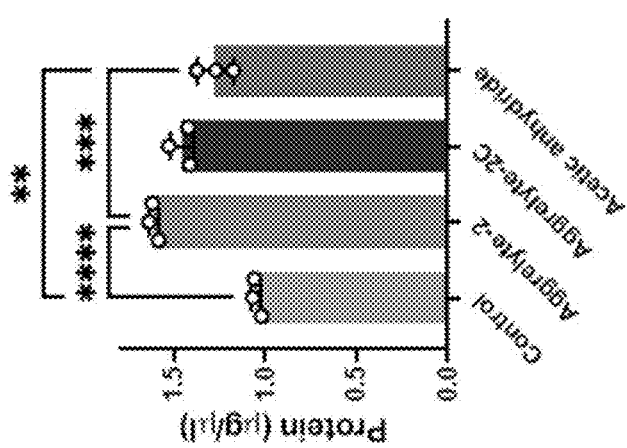

Results are presented in FIGS. 8A and 8B. Although acetic anhydride was a better acetylating agent than Aggrelyte-2 (FIG. 8B), Aggrelyte-2 was significantly (p<0.001) 1.3 times better than acetic anhydride in solubilizing WI proteins (FIG. 8A). p<0.01, *p<0.001, and ****p<0.0001.

Example 8: Crystallin Levels in Solubilized Human Lens Proteins

The contents of crystalline proteins [αA-crystallin (αAC), αB-crystallin (αBC), β-crystallin (βC), and γ-crystallin (γC)] in the solubilized proteins of three human lenses (68-, 73-, and 75-year-old) treated with either Aggrelyte-2 or Aggrelyte-2C (500 µM) from Example 4 were determined by Western blot analysis as described for Example 5. Membranes were incubated with antibodies against αAC (1:14,000 dilution; Enzo Life Sciences, Catalog #ADI-SPA-221D), αBC (1:700,000 dilution; University of Iowa), βC (1:14,000 dilution; Santa Cruz Biotechnology, Catalog #sc-22745), and γC (1:7,000 dilution; Santa Cruz Biotechnology, Catalog #sc-22746). The secondary antibodies were HRP-conjugated anti-mouse IgG for αBC and HRP-conjugated rabbit IgG (Cell Signaling Technology, Catalog #7074S) for αAC, βC, and γC. According to the supplier, the RC antibody detects mostly βB1-crystallin and, to a lesser extent, βA1/3, βA2, βA4, βB2, and βB3-crystallin. The γC antibody reacts with γA, γB, γC, γD, γE, and γF-crystallin.

Figures 9A, 9B, 9C, 9D:
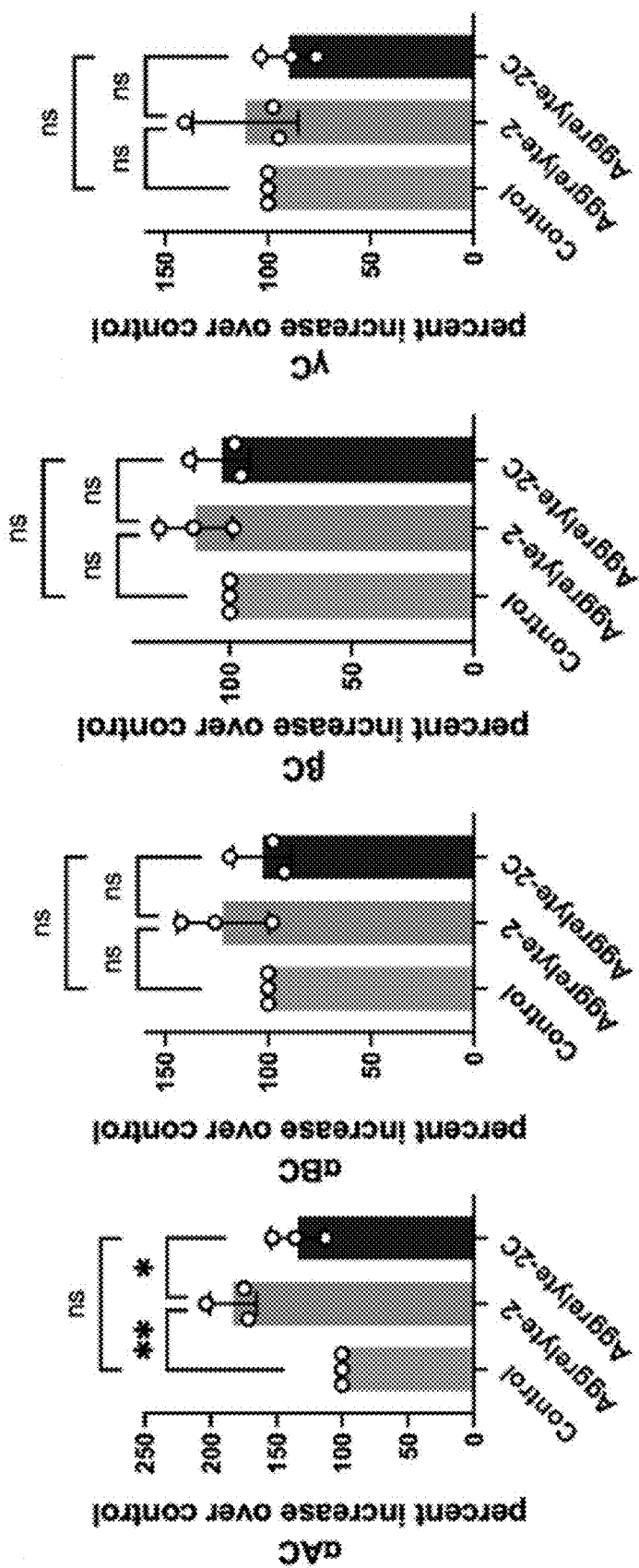
FIGS. 9A-9D are bar graphs showing the effects of Aggrelyte-2 and Aggrelyte-2C on acetylation of human lens crystallin proteins [αAC (FIG. 9A), αBC (FIG. 9B), 3C (FIG. 9C) and γC (FIG. 9D)] generated from Western blot densitometric analysis.

Results are shown in FIGS. 9A-9D in which bar graphs represent the mean±S.D. of n=3 measurements. The levels of αAC were 1.8-fold higher (p<0.01) in the Aggrelyte-2-treated samples than in the Controls, and 1.3-fold higher (p<0.05) than in the Aggrelyte-2C-treated samples (FIG. 9A). The levels of αBC were 1.2-fold higher (not significant) in Aggrelyte-2-treated samples than in the Controls, and 1.1-fold higher (not significant) than in the Aggrelyte-2C-treated samples (FIG. 9B). The levels of βC (FIG. 9C) and γC (FIG. 9D) were slightly but not significantly higher in the Aggrelyte-2-treated samples than in the Controls. Aggrelyte-2C had no effect on the levels of either βC or γC. α-Crystallins may be a target of Aggrelyte-2-mediated acetylation in human lenses. *p<0.05, **p<0.01, and ns=not significant.

Example 9: Effects of Aggrelyte-2 and Aggrelyte-2C on Protein Thiol Levels

Protein thiol content in the solubilized protein from WI protein from aged lenses (58 to 69 years old) was evaluated. Immediately after treatment with aggrelytes as described in the foregoing examples, 0.15 mL samples were filtered through 10 kDa cutoff centrifugal filters at 4° C. Centrifugal filtration was repeated twice by adding 0.4 mL of 50 mM $N_2$-bubbled sodium phosphate buffer to the retentate each time. Ten micrograms of protein from the final retentate was used for thiol content estimation using a Thiol Quantification Assay Kit (Abcam, Cambridge, MA) using reduced GSH as the standard.

Figure 10B:
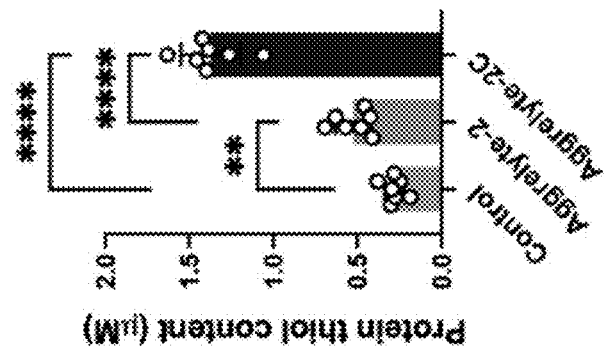
FIGS. 10A and 10B are bar graphs showing the effects of Aggrelyte-2 and Aggrelyte-2C on protein thiol levels.
Figure 10A:
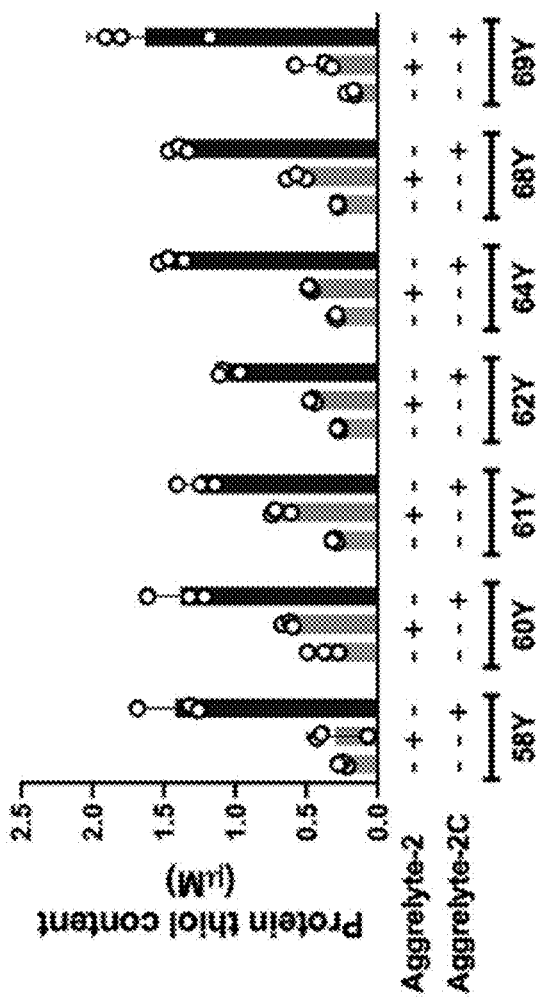

Results are presented in FIGS. 10A and 10B, in which the data are the mean±S.D. for each sample processed three times separately and analyzed. A combined plot of the mean values of the three analyses of each sample is shown in FIG. 10B. In the control samples, the thiol content was 0.2-0.4 µM. In the Aggrelyte-2-treated samples, the thiol content was 0.3-0.7 µM, which was significantly (p<0.01) higher (1.9-fold) than in the untreated controls. In the Aggrelyte-2C-treated samples, the thiol content was significantly (p<0.0001) higher (4.9-fold) than in the controls and also significantly (p<0.0001) higher (1.1-1.6 µM, a 2.6-fold increase) than in Aggrelyte-2-treated samples.

Together, these results suggest that aggrelytes can reduce disulfide bonds in proteins. In view of the greater ability of Aggrelyte-2 to solubilize WI proteins (Example 4), disulfide bonds are not the sole contributor to protein insolubility in human lenses.

Example 10: Effects of Aggrelyte-2 and Aggrelyte-2C on the Stiffness and Axial Strain of Ex Vivo Mouse and Human Lenses All animal experiments adhered to the ARVO Statement for the Use of Animals in Ophthalmic and Vision Research and were reviewed and approved by the Institutional Animal Care and Use Committee (IACUC) of the University of Colorado, Aurora.

In this example, the lenses were dissected from the eyes of mice (C57BL/6J, 5-8 months old, Jackson Laboratories, Stock No. 000664, n=4-5) by a posterior approach and incubated without ("Control") or with Aggrelyte-2 or Aggrelyte-2C (1 mM) for 24 hours in serum-free and phenol-red-free MEM (297 mOsm) at 37° C. Lens stiffness was measured as previously described in Baradia, H. et al., (2010) Exp. Eye Res. 91, 300-307. Briefly, the lens was placed on a flat platform with the anterior side facing up, and a load was applied to the top of the lens at 100 mg increments for mouse lenses and at 250 mg increments for human lenses. The displacement in the lens axial diameter (in μm or mm) was measured using MATLAB software developed by Dr. Adrian Glasser, UK, and plotted against the load applied. The displacement at a specific load was used to determine differences in lens stiffness between the untreated control and aggrelyte-treated lenses.

Freshly obtained human lenses (42-68 years old, n=10-12) were incubated with or without Aggrelyte-2 or Aggrelyte-2C (1 mM) for a total of 72 h in phenol red-free MEM with a change in media containing freshly dissolved aggrelytes every 24 h. One lens from each donor pair was used as the control, and the other was treated with aggrelyte. After incubation, the lens stiffness was measured as described above. Axial strain was also calculated based on the following formula:

$$\frac{\text{(diameter of the lens after the load applied} - \text{initial diameter of the lens)}}{\text{initial diameter of the lens}}$$

Figure 11B:
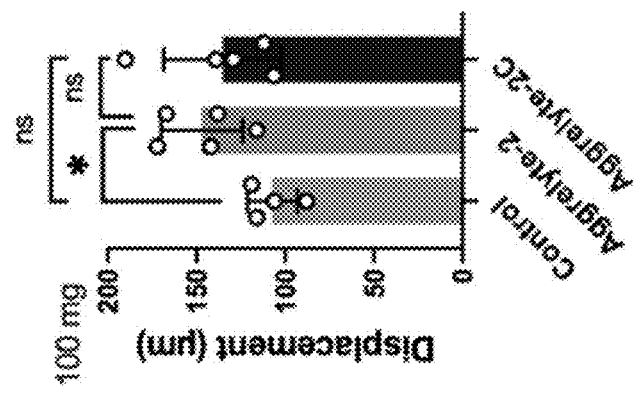
Figure 11A:
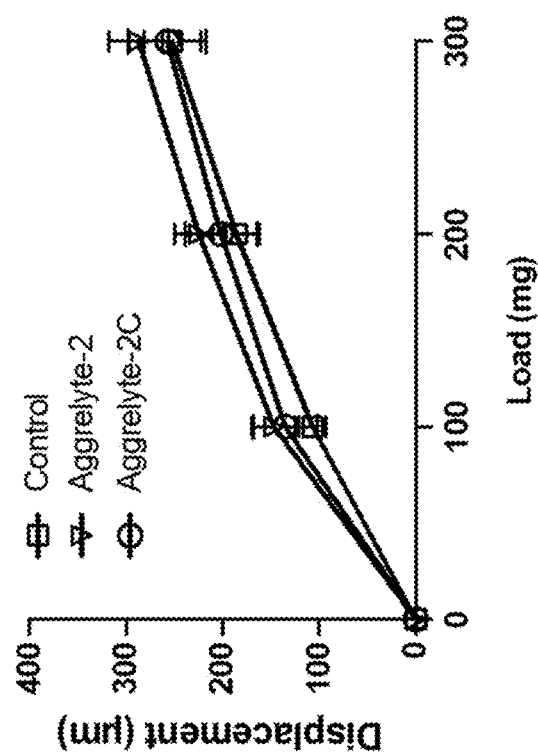

Results are presented in FIGS. 11A-11H in which the bar graphs represent the mean±S.D. of measurements, and *=p<0.05, **=p<0.01, and ns=not significant. Aggrelyte-2 significantly (p<0.05) reduced the stiffness in 6-month-old mouse lenses subjected to a 100 mg load compared to untreated control lenses (FIG. 11B). The displacement by Aggrelyte-2 was 8.7% greater than that by Aggrelyte-2C, but not significantly greater.

In human lenses (42-68 years), Aggrelyte-2 treatment resulted in increased displacement compared to untreated controls (FIGS. 11C-11E). At loads of both 500 mg (FIG. 11D) and 1000 mg (FIG. 11E), treatment with Aggrelyte-2 significantly (p<0.01) reduced lens stiffness compared to controls. Treatment with Aggrelyte-2C did not demonstrate significant effects on displacement compared to untreated controls (FIGS. 11F-11H).

Figure 12C:
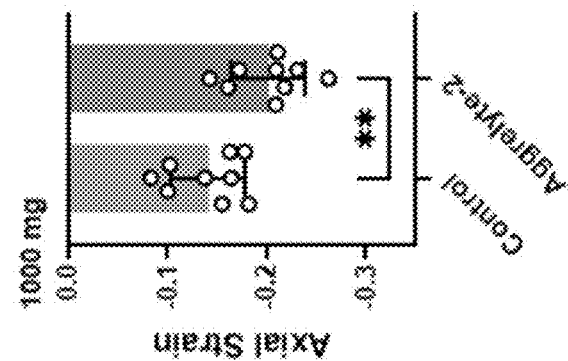
FIGS. 12A-12C are bar graphs showing the effects of Aggrelyte-2 and Aggrelyte-2C on mouse (FIG. 12A) and human (FIGS. 12B and 12C) lens axial strain.
Figure 12B:
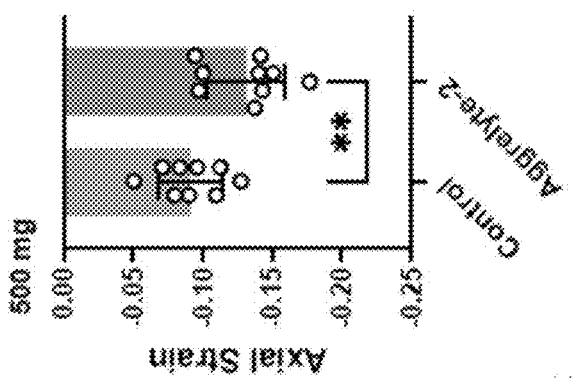
Figure 12A:
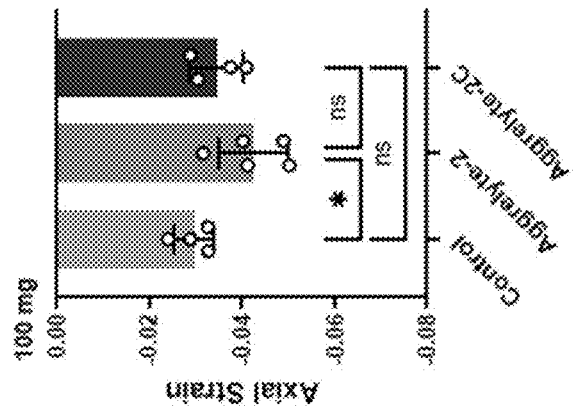

FIG. 12A shows that, at a 100 mg load, treatment with Aggrelyte-2 significantly (p<0.05) reduced the axial strain of the mouse lenses compared to controls. Treatment with Aggrelyte-2 also significantly (p<0.01) reduced the axial strain compared to controls at both 500 mg (FIG. 12B) and 1000 mg (FIG. 12C) loads. *=p<0.05, **=p<0.01, ns=not significant.

Aggrelyte-2C did not have a significant effect on axial stiffness for either mouse or human lenses (data not shown).

Together, these results demonstrated that Aggrelyte-2 can reduce the stiffness of aged mouse and human lenses.

Example 11: Ability of Aggrelyte-2 and Aggrelyte-2C to Solubilize Proteins from Human Lenses Water soluble (WS) proteins were obtained from both mouse and human lenses. For mouse lenses, WS protein was obtained by homogenizing each mouse lens in 0.2 mL of PBS, followed by centrifugation at 20,000×g for 20 min at 4° C. (See Example 12 for the investigation of WS proteins from mouse lenses.) For human lenses, the lenses of Example 10 were decapsulated, transferred to a 5- or 10-mL round bottom flask containing 1 mL of 50 mM phosphate buffer, pH 7.4, and stirred using a magnetic stir bar to solubilize the protein from the cortex of the lens. The remaining nucleus was homogenized in 1 mL phosphate buffer. Both cortical and nuclear protein extracts were centrifuged at 20,000×g for 20 min at 4° C. to obtain the soluble protein in the supernatant. In another set of experiments, human lenses (42-64 years), following incubation with aggrelytes as described in the foregoing examples, were each homogenized with 1.5 mL 50 mM phosphate buffer, pH 7.4. The homogenate was centrifuged at 20,000×g for 20 min to obtain a supernatant. Protein in the supernatant was evaluated to determine the effect of aggrelyte treatment on the soluble protein content in the lens.

Figure 13:
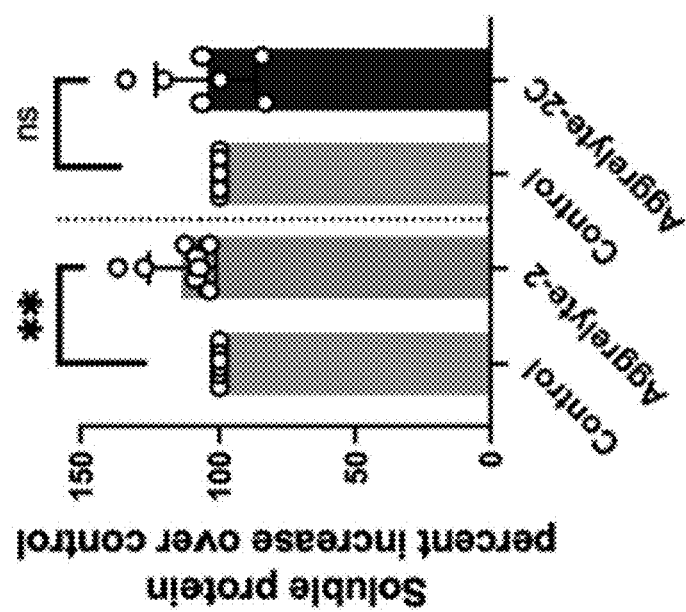
FIG. 13 is a bar graph showing the effects of Aggrelyte-2 and Aggrelyte-2C on the water-soluble protein content in human lenses.

Results are shown for human lenses in FIG. 13, in which the bar graphs represent the mean±S.D. of measurements, and *=p<0.05, **=p<0.01, and ns=not significant. The WS content was 13.2% higher (p<0.01) in the Aggrelyte-2-treated human lenses than in the untreated controls (contralateral lenses). The WS content of Aggrelyte-2C-treated lenses was 4.6% higher (not significant) than in the untreated controls. The results demonstrate that Aggrelyte-2, but not Aggrelyte-2C, was able to increase protein solubility in human lenses.

Example 12: Effects of Aggrelyte-2 and Aggrelyte-2C on Levels of Acetylated Proteins in Mouse and Human Lenses (Western Blot Analysis)

Mouse and human lenses were treated with aggrelytes as described in Example 10. Water-soluble proteins from mouse and human lenses were obtained as described in Example 13. Effects of aggrelyte treatment on AcK-bearing proteins in the WS fractions were evaluated by Western blot analysis as described in Example 5. For Western blotting, 10-20 μg of protein from each lens sample was used and each sample was separately processed three times and analyzed.

Figures 14A, 14B, 14C, 14D, 14E:
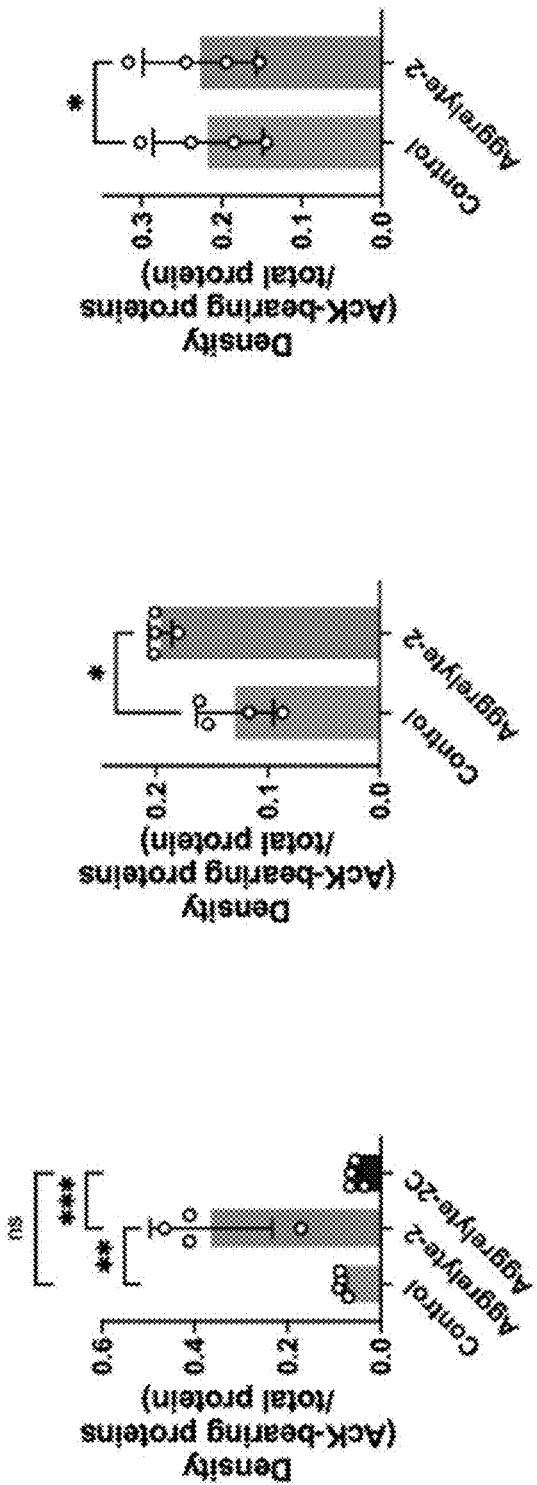
FIGS. 14A-14E are bar graphs showing the effects of Aggrelyte-2 and Aggrelyte-2C on acetyllysine levels evaluated by Western blot analysis and densitometry. Mouse lenses are shown in FIG. 14A.

Densitometric plots from Western blots of WS proteins are shown in FIG. 14A-E. The bar graphs represent the mean±S.D. of n=4 measurements, and *=p<0.05, =p<0.01, *=p<0.001, and ns=not significant. Mouse lenses treated with Aggrelyte-2 showed significantly higher AcK modifications than in the untreated controls (p<0.01) as well as in the Aggrelyte-2C-treated lenses (p<0.001) (FIG. 14A).

Significantly higher (p<0.05) AcK content was also observed in both the cortical protein fraction from human lenses (FIG. 14B), and the nuclear fraction (FIG. 14C). The AcK levels in the cortical and nuclear proteins of Aggrelyte-2C-treated lenses were not statistically different than those in the untreated controls (FIGS. 14D and 14E).

Together, the results demonstrate that treatment with Aggrelyte-2 significantly increases the levels of AcK-bearing proteins in mouse and both the nuclear and cortical proteins from human lenses.

Example 13: Effects of Aggrelyte-2 and Aggrelyte-2C on Levels of Acetylated Proteins in Mouse and Human Lenses (LC-MS/MS Analysis)

Mouse and human lenses were treated with aggrelytes as described in Example 10. Water-soluble proteins from mouse and human lenses were obtained as described in Example 13. Effects of aggrelyte treatment on AcK-bearing proteins in the WS fractions were evaluated by LC-MS/MS analysis as described in Example 6.

Figures 15A, 15B, 15C:
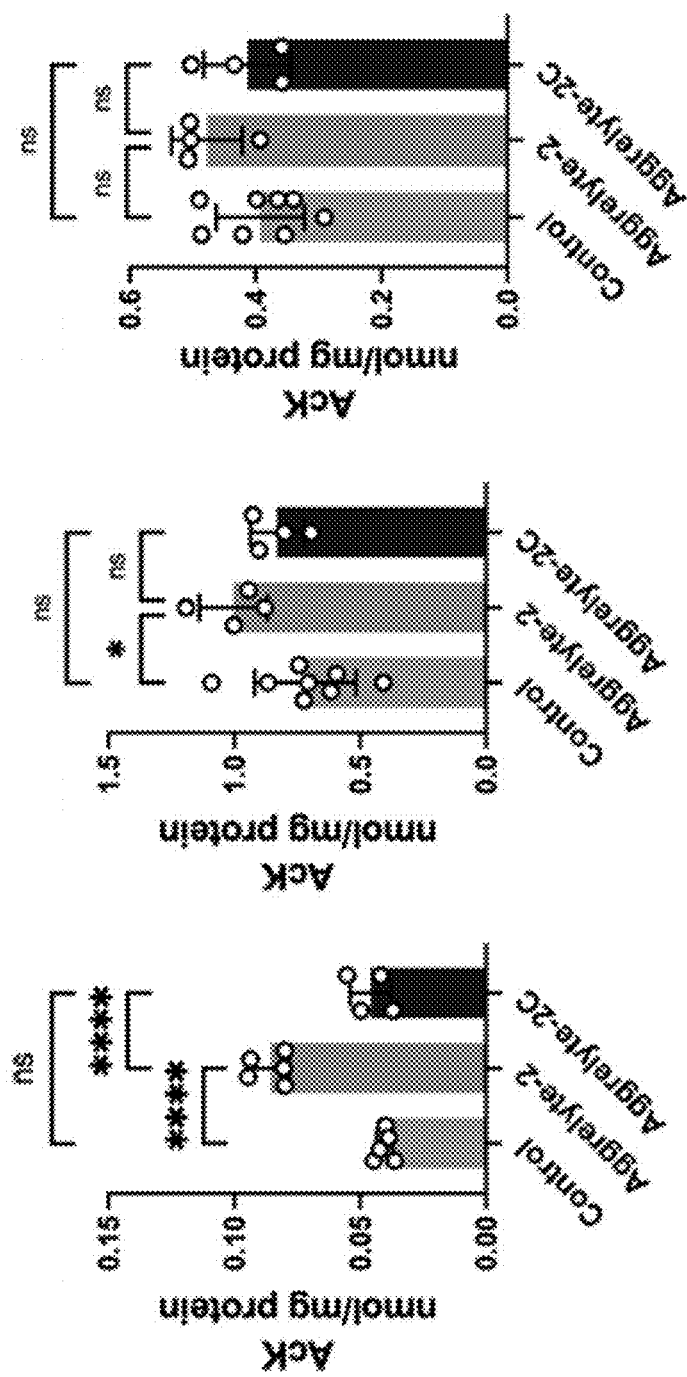
FIGS. 15A-15C are bar graphs showing the effects of Aggrelyte-2 and Aggrelyte-2C on acetyllysine levels evaluated by LC-MS/MS. Mouse lenses are shown in FIG. 15A.
Figure 16A:
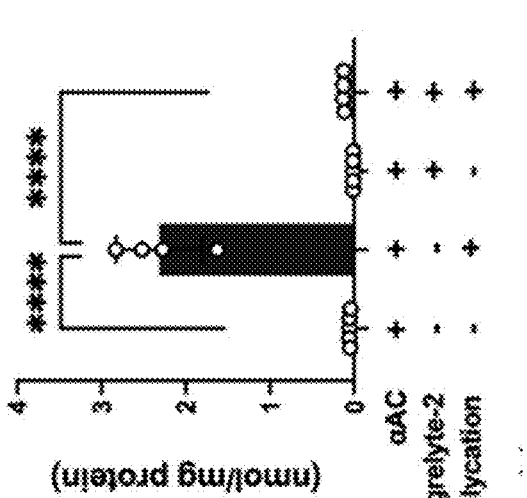
FIGS. 16A-16D are bar graphs showing the effects of Aggrelyte-2 on advanced glycation end product (AGE) formation from human recombinant αAC (FIGS. 16A and 16B) and TDC (FIGS. 16C and 16D).
Figure 16B:
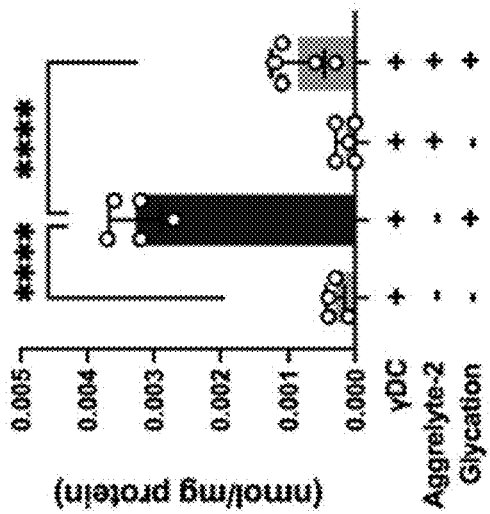
Figure 16C:
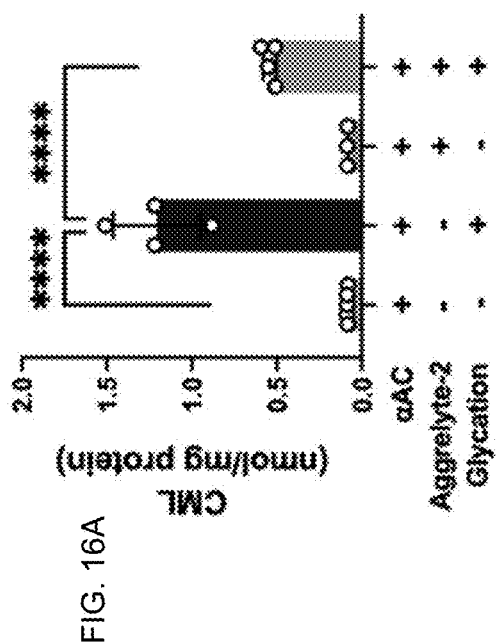
Figure 16D:
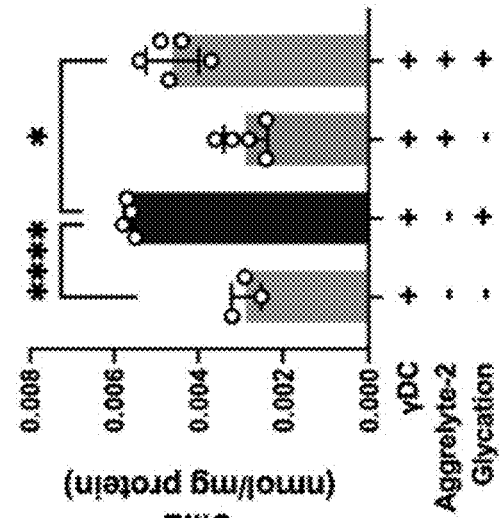

Results are shown in FIG. 15A-C, in which the bar graphs represent the mean±S.D. of n=3-5 measurements, and *=p<0.05, ****=p<0.0010, and ns=not significant. Mouse lenses treated with Aggrelyte-2 showed significantly higher AcK modifications than in the untreated controls (p<0.0001) as well as in the Aggrelyte-2C-treated lenses (p<0.0001) (FIG. 15A).

Significantly higher (p<0.05) AcK content was also observed in the cortical protein fraction from human lenses (FIG. 15B) compared to untreated controls. In the nuclear fraction, Aggrelyte-2 treatment resulted in an AcK increase that was not statistically greater than untreated controls (FIG. 15C). In contrast, Western blot analysis showed a statistically significant increase in AcK levels in the nuclear proteins of aggrelyte-2 treated lenses when compared to the controls (FIG. 14C). The discrepancy may be due to poor enzymatic digestion of the highly cross-linked nuclear proteins conducted prior to LC-MS/MS analysis.

Nonetheless, the results of Examples 11-13 collectively suggest that Aggrelyte-2 permeates lenses (cortex, and possibly nucleus in the case of the human lenses), acetylates lysine residues in proteins, and promotes the solubility of proteins.

Example 14: Identification of AcK Sites in Proteins of Aggrelyte-Treated Lens The AcK modification sites and relative levels at those sites in the Aggrelyte-2-treated and untreated (control) human lens cortical proteins were evaluated in the lens (from a 49-year donor) that had the largest overall AcK differential measured by Western blot analysis (blot not shown; densitometric summary in FIG. 14B) and LC-MS/MS (FIG. 15B). Each sample (315 µg) was spiked with 200 ng of acetylated bovine serum albumin (AcBSA) protein standard, reduced, alkylated, and digested with trypsin using a urea-based method and then desalted using a C18 resin before being lyophilized. The samples were then immunoprecipitated according to the manufacturer's protocol for the PTMScan Acetyl-Lysine Motif Kit No. 13416 (Cell Signaling Technology). Peptides were purified with a Pierce C18 spin column (Thermo Fisher Scientific) and dried in a Speed Vac concentrator at 45° C. The peptides were resuspended in 3% acetonitrile in 0.1% formic acid for MS analysis.

The enriched AcK-bearing peptides were loaded onto a 2 cm PepMap 100 nanoviper trapping column and chromatographically resolved with a 0.075×250 mm, 2.0 m Acclaim PepMap RSLC reversed-phase nanocolumn (Thermo Scientific) using a 1290 Infinity II LC system equipped with a nanoadapter (Agilent). The mobile phase consisted of water+0.1% formic acid (A) and 90% aqueous acetonitrile+0.1% formic acid (B). Samples were loaded onto the trapping column at 3.0 µL/min for 3.5 min under initial conditions before being chromatographically separated at an effective flow rate of 330 nL/min using a gradient of 3-8% B over 3 min, 8-30% B over 33 min, and 30-40% B over 4 min at 40° C. The gradient was followed by a column wash at 75% B for 5 min. Data were collected using a 6550 Q-TOF equipped with a nanosource (Agilent Technologies) operated using intensity-dependent CID MS/MS to generate peptide identifications. MS/MS data were collected in positive ion polarity over a mass range of 290-1700 m/z at a scan rate of 8 spectra/second for MS scans and a mass range of 50-1700 m/z at a scan rate of 3 spectra/second for MS/MS scans. All charge states, except singly charged species, were allowed during MS/MS acquisition.

Tandem mass spectra were extracted, searched, and summarized using PEAKS X+ Studio 10.5 software (Bioinformatics Solutions Inc., Waterloo, Ontario). The spectra were searched against the UniProtKB SwissProt [2022_02] *Homo sapiens* database, allowing for up to three missed semitryptic cleavages with fixed carbamidomethylation of cysteine and a maximum of four variable modifications of deamidation of asparagine and glutamine, oxidation of methionine and/or acetylation of lysine per peptide. The allowed monoisotopic peptide mass tolerance was ±15.0 ppm, and the MS/MS tolerance was ±0.05 da. A false discovery rate (FDR) filter of 0.5% was used corresponding to a −10 log P score ≥19.3.

The MS-only level data from the LC-MS/MS analyses were extracted and aligned using Profinder V.B.10.01 software (Agilent Technologies). Retention times, neutral masses, and chemical formulas generated from identified acetyl peptides were used to perform batch-targeted feature extraction. Data were extracted with an ion count threshold of two or more ions, 5000 counts, and a score threshold of 70. The score was based on the quality of the mass accuracy, isotope abundances, and isotope spacing of compounds based on the chemical formula of the target peptides within a specified retention time window. Using the peptide isotope model, charge states 2-6 were allowed with $H^+$ and $Na^+$ charge carriers. The retention time window and mass window alignment tolerances were set to 0.4 min and 10 ppm, respectively. The extracted peptide peak areas were then used to determine a fold change value in the treated vs. control samples to help identify potential AcK sites that may be affected by aggrelyte-2. Due to a lack of statistical power, a three-fold change filter was used as a sufficient cutoff to identify potential AcK sites of interest. The list of AcK sites that passed the three-fold change cutoff was further curated to include only those AcK sites for which all corresponding peptides with the same AcK site had a three-fold change or greater when summed and averaged together.

Samples were also searched using the UniProtKB SwissProt *Bos taurus* database to identify peptides from the acetylated BSA standard spiked-in at the beginning of sample preparation. All other search and MS-only level extraction parameters were unchanged compared to the SwissProt *Homo sapiens* workflow. Extracted acetylated BSA peptide peak areas were summed and used to determine a fold change value in treated vs. control samples.

Three hundred fifteen AcK-bearing peptides that passed the 0.5% FDR filter were identified, corresponding to 170 AcK sites and 59 proteins. Table 1 below lists 14 AcK-sites, corresponding to 20 AcK peptides and 11 proteins, identified in the Aggrelyte-2-treated lens that were at least 3-fold greater than similar AcK sites in the untreated control lens. Among those, six AcK sites from six proteins were at least 5-fold greater than the peptides from untreated control lenses. AcK at K88 in αAC and K370 in the α1A-chain of tubulin, each denoted with *) were not detected in the control lens but were prominent in the Aggrelyte-2-treated lens. Both lens samples had been spiked with 200 ng of AcBSA protein to ensure that fold change values for identified AcK sites were not due to the sample workup or instrument errors. Seventeen AcBSA peptides were identified in both treated and control lenses and, when summed, yielded a 1.05-fold change in the treated vs. control lenses. There was very little change in the overall AcBSA signal, indicating that the AcK-bearing peptide measurements are a true reflection of the acetylation levels in the treated and control lenses.

TABLE 1

Identification of AcK Sites in Proteins of Aggrelyte-2-Treated Lens

| Protein Name | Uniprot Accession # | AcK site | Peptide count AcK site | Aggrelyte-2 treated Area | Control Area | Fold Change (Aggrelyte-2 vs Control) [Total Sum] |
|---|---|---|---|---|---|---|
| AlphaA-crystallin | P02489 | K88 | 1 | 1.11E+05 | | * |
| Tubulin alpha-1A chain | Q71U36 | K370 | 1 | 4.24E+04 | | * |
| BetaB2-crystallin | P43320 | K42 | 1 | 6.98E+05 | 2.71E+04 | 25.80 |
| Phakinin | Q13515 | K400 | 1 | 2.21E+05 | 1.52E+04 | 14.48 |
| Retinal dehydrogenase 1 | P00352 | K495 | 1 | 9.11E+04 | 9.99E+03 | 9.12 |
| AlphaB-crystallin | P02511 | K174 | 3 | 5.84E+06 | 7.88E+05 | 7.41 |
| Filensin | Q12934 | K360 | 1 | 1.16E+05 | 2.94E+04 | 3.94 |
| Cytidine deaminase | P32320 | K51 | 1 | 7.26E+05 | 1.99E+05 | 3.66 |
| AlphaB-crystallin | P02511 | K72 | 1 | 6.31E+05 | 1.77E+05 | 3.56 |
| Actin cytoplasmic 1 | P60709 | K213 | 1 | 1.03E+05 | 2.92E+04 | 3.53 |
| Actin cytoplasmic 1 | P60709 | K61 | 1 | 7.63E+04 | 2.19E+04 | 3.48 |
| Peroxiredoxin-6 | P30041 | K56 | 2 | 5.83E+05 | 1.79E+05 | 3.26 |
| Glyceraldehyde-3-phosphate dehydrogenase | P04406 | K263 | 1 | 1.04E+05 | 3.27E+04 | 3.18 |
| AlphaA-crystallin | P02489 | K70 | 4 | 8.80E+06 | 2.81E+06 | 3.13 |
| Acetylated Bovine Serum Albumin Standard Spike at 200 ng in each sample | N/A | N/A | 17 | 3.68E+07 | 3.85E+07 | −1.05 |

Example 15: Effect of Aggrelyte-2 on AGE Formation in Lens Proteins

To investigate the effects of Aggrelyte-2 on advanced glycation end product (AGE) formation, human recombinant αAC (3 mg/mL) or γD-crystallin (γDC, 2 mg/mL) in PBS was treated with or without aggrelyte-2 (10 mM for αAC and 1.25 mM for γDC) for 24 h, dialyzed against 100 mM sodium phosphate buffer pH 7.4 for 16 h and incubated with or without a glycating mixture (2 mM ascorbate, 25 mM D-glucose and 250 μM methylglyoxal) in 100 mM sodium phosphate buffer pH 7.4 for 5 days (after adding 0.002% sodium azide) at 37° C. The incubated proteins were dialyzed against PBS for 16 h, treated with 100 mM sodium borohydride for 1 h at room temperature, and acid hydrolyzed. Two AGEs, $N^\epsilon$-carboxymethyllysine (CML) and $N^\epsilon$-carboxyethyllysine (CEL), were measured by LC-MS/MS as described above. Each sample was separately processed 3-4 times.

Results are shown in FIGS. 16A-16D, in which bar graphs represent the mean±S.D. of 3-4 measurements, and *=p<0.05, ****=p<0.0001, and ns=not significant. The levels of both CML (FIGS. 16A and 16C) and CEL (FIGS. 16B and 16D) in both human recombinant αAC (FIGS. 16A and 16B) and γDC (FIGS. 16C and 16D) increased upon glycation. However, treatment of proteins with Aggrelyte-2 prior to glycation significantly reduced (p<0.0001) the levels of both CML and CEL.

These results demonstrate that Aggrelyte-2 inhibits AGE formation in lens proteins, including through AcK formation.

Example 16: Synthesis of Aggrelyte-2A

N-acetylation of L-cysteine methyl ester (500 mg, 2.91 mmol; Sigma Aldrich Catalog #410209) was performed by mixing with tert-butylacetyl chloride (364 μl, 2.62 mmol) in N,N-diisopropylethylamine (456 μl, 2.62 mmol) and stirring overnight at room temperature. The reaction mixture was subjected to prep HPLC on a C18-Safar Biotage 100A° column (solvent A: water+0.1% trifluoroacetic acid (TFA); solvent B: 95% acetonitrile in water+0.1% TFA; 10-95% gradient; 0-7 min: 10% B, 7-17 min: 10-100% B; flow rate 15 mL/min). The column effluent was monitored at 215 nm, and the product that eluted at a retention time (Rt) of 9.7 minutes was collected and lyophilized. S-acetylation of the product was performed by mixing it with acetyl chloride (242 μl, 1.75 mmol) and triethylamine (243 μl, 1.75 mmol) in 20 mL of dichloromethane and stirring at room temperature for 12 h. The solvent was removed under vacuum, and the resulting gummy residue was then purified using prep HPLC on a C18-Safar Biotage 100A° column (solvent A: water+0.1% TFA; solvent B: 95% acetonitrile in water+ 0.1% TFA; 10-95% gradient; 0-7 min: 10% B, 7-17 min: 10-100% B; flow rate 15 mL/min). The column effluent was monitored at 215 nm, and the product eluting at Rt of 12.9 minutes was collected and lyophilized. The structure of the compound was confirmed by $^1$H-NMR 400 MHz in CDCl$_3$. δ 1.03 (s, 9H, CH$_3$), 2.10 (s, 2H, CH$_2$), 2.34 (s, 3H, CH$_3$CO), 3.35 (m, 2H, CH$_2$), 3.75 (s, 3H, CH$_3$OCO), 4.76 (m, 1H, CH), 6.28 (bs, 1H, CONH). The structure of the produced compound, named Aggrelyte-2A, is shown in FIG. 1B.

Example 17: Toxicity Studies of Aggrelyte-2A

Figure 17A:
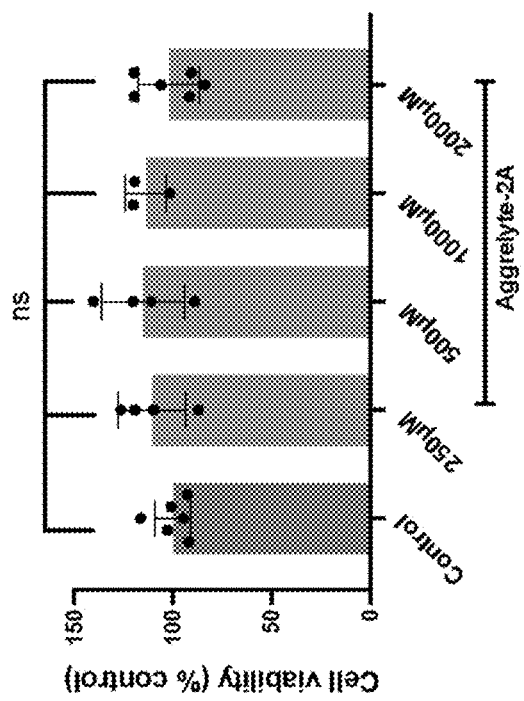
FIGS. 17A and 17B are bar graphs showing the effects of Aggrelyte-2A on mouse (FIG. 17A) and human (FIG. 17B) lens epithelial cell viability.
Figure 17B:
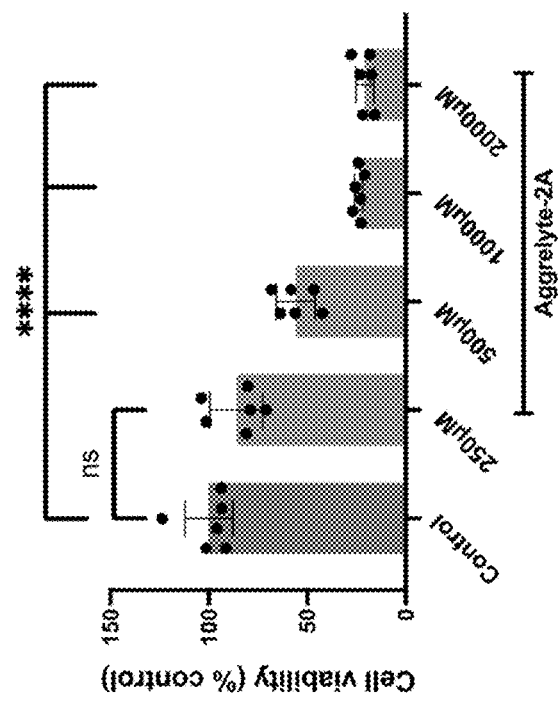

Mouse lens epithelial cells (primary cells from lenses of 1-month-old C57BL/6J mice; passages: 3-5) were incubated with 0 µM ("Control") to 2000 µM Aggrelyte-2A for 24 hours. Primary human lens epithelial cells (isolated from a 34-year-old donor; passages: 3-5) were incubated with 0 µM ("Control") to 2000 µM Aggrelyte-2A for 48 hours, with a change of media containing freshly dissolved Aggrelyte-2A after 24 hours. Cell viability was measured using the MTT assay. The results are shown in FIG. 17A (mouse lens epithelial cells) and FIG. 17B (human lens epithelial cells). All data, for Examples 17-22, are expressed as mean±standard deviation (SD) from at least triplicate samples. Unpaired Student's t-test was used to calculate the significance of difference between samples.

The data demonstrate that Aggrelyte-2A was not toxic to mouse lens epithelial cells at a concentration of up to 1000 µM after exposure for 24 hours and not toxic to human lens epithelial cells at a concentration of up to 250 µM after exposure for 48 hours.

Example 18: Effects of Aggrelyte-2 and Aggrelyte-2A on the Stiffness of Ex Vivo Mouse Lenses In this example, the lenses were dissected from the eyes of mice (C57BL/6J, 3-6 months old, Jackson Laboratories, Stock No. 000664) by a posterior approach and incubated without ("Control") or with Aggrelyte-2 or Aggrelyte-2A (1 mM) for 24 hours in serum-free and phenol-red-free MEM (297 mOsm) at 37° C. Lens stiffness was measured as in Example 10, except that the load was applied at 50 mg increments.

Results are presented in FIGS. 18A-18C. Aggrelyte-2 and Aggrelyte-2A performed comparably. Each aggrelyte reduced the stiffness of mouse lenses ex vivo by approximately 20% (not significant). The ability of an aggrelyte to reduce lens stiffness may help improve the ability of a lens to accommodate and/or may treat presbyopia.

Example 19: Effects of Aggrelyte-2 and Aggrelyte-2A on Levels of Acetylated Proteins in Mouse Lenses The lenses from Example 18 were homogenized using N2-bubbled 50 mM phosphate buffer, pH 7.4 (0.4 mL per lens), in a hand-held motorized homogenizer. The homogenate was centrifuged at 20,000×g for 20 minutes at 4° C. The resulting supernatant was collected, and its protein content was measured using BCA Protein Assay Kit using BSA as the standard. The soluble protein was subjected to 12% SDS-PAGE under denaturing conditions and the proteins were electrophoretically transferred to a nitrocellulose membrane and blocked with 5% nonfat dry milk. The membrane was then incubated with a monoclonal antibody against N-acetyllysine (AcK antibody @ 1:5,000 dilution; Cell Signaling Technology Catalog #9681S) for 16 hours, followed by horseradish peroxidase (HRP)-conjugated goat anti-mouse IgG (1:5,000 dilution; Cell Signaling Technology Catalog #7076S) for 1 hour. Chemiluminescence was detected using the Enhanced Chemiluminescence Detection Kit. The membrane was stained with Ponceau-S to visualize the proteins and normalize acetyllysine (AcK)-bearing protein to total protein load.

Figure 19:
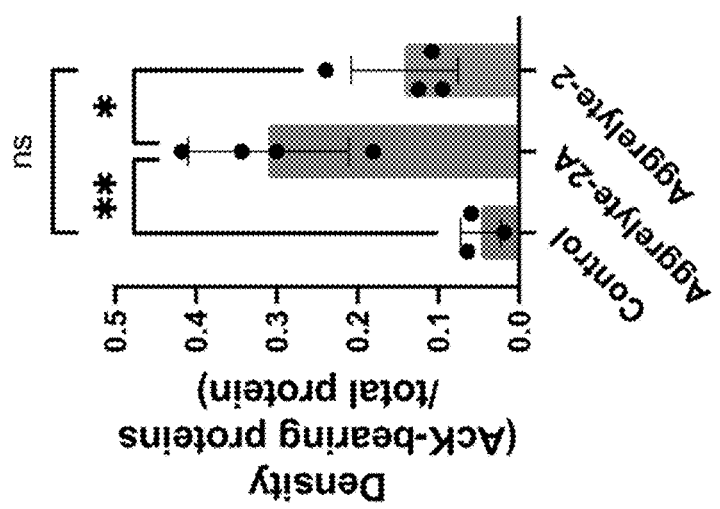
FIG. 19 is a bar graph showing the effects of Aggrelyte-2 and Aggrelyte-2A on acetylation of mouse lens proteins.

The results are shown in FIG. 19. Both Aggrelyte-2 and Aggrelyte-2A increased the density of acetylated mouse lens proteins compared to untreated control lenses. The results demonstrate that Aggrelyte-2A increased the density of acetyl-bearing proteins by 5-fold compared to untreated control lenses (**=$p<0.01$). Aggrelyte-2 increased the density of acetyl-bearing proteins by 2-fold compared to untreated control lenses (*=$p<0.05$). The results demonstrate that Aggrelyte-2A increased the density of acetyl-bearing proteins by at least 50% compared to Aggrelyte-2 (*=$p<0.05$).

The ability of an aggrelyte to acetylate lens proteins may help solubilize aggregated lens proteins and decrease lens stiffness.

Example 20: Effects of Topically Administered Aggrelyte-2A on Stiffness, Acetylation Levels, and Thiol Content of Mouse Lenses Five C57BL/6J male or female six-month-old mice were acclimatized at the University of Colorado. A 40 mM solution of Aggrelyte-2A was prepared in a liquid formulation that consisted of benzalkonium chloride (0.001%), $NaH_2PO_4 \cdot H_2O$ (0.269%), $Na_2HPO_4$ (0.433%), hypromellose (0.2%), and NaCl (0.5%). Aggrelyte-2A in the formulation (5 µl) was applied to the right eye twice daily (8 AM and 4 PM) to unanesthetized animals for four weeks. The left eye received only the formulation (5 µl) ("Vehicle" or "Control"). After treatment, the animals were euthanized by $CO_2$ asphyxiation. The eyes were enucleated, and the lenses were removed immediately by a posterior approach and placed in fresh PBS. The stiffness of the lenses was measured using a computer-controlled lens squeezer. The AcK-bearing protein levels of the lenses were measured by Western blotting. The protein-thiol content of the lenses was measured using a Thiol Quantification Assay Kit from Abcam, using reduced GSH as the standard.

Figure 20:
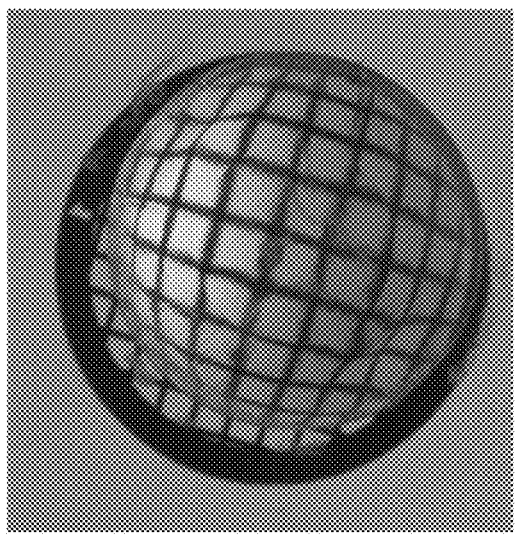
FIG. 20 shows the effects of topically applied Aggrelyte-2A on mouse lens transparency.
Figure 20:
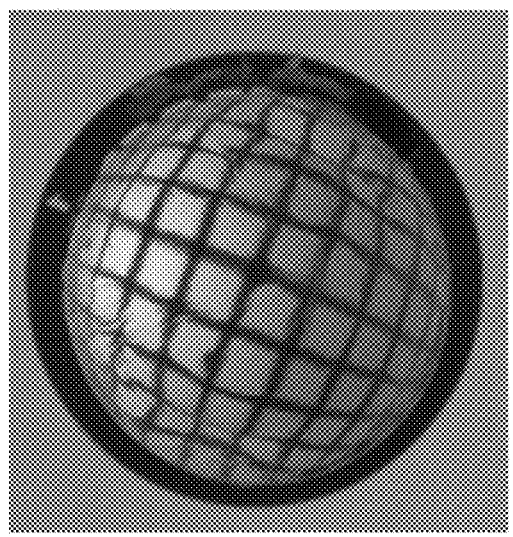
Figure 23:
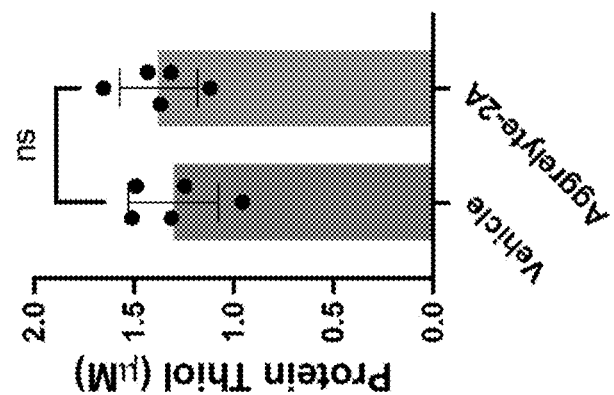
FIG. 23 is a bar graph showing the effects of topically applied Aggrelyte-2A on thiol content of mouse lens proteins.
Figure 22:
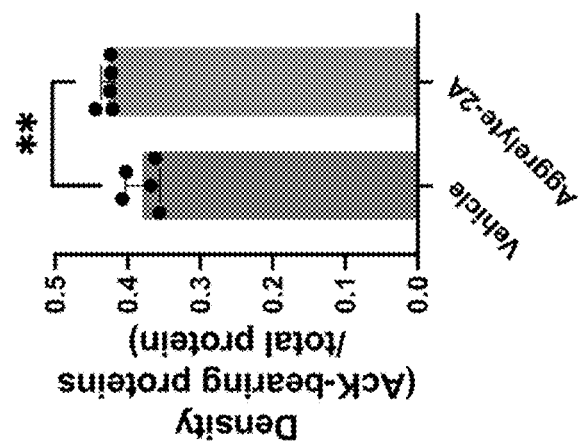
FIG. 22 is a bar graph showing the effects of topically applied Aggrelyte-2A on acetylation of mouse lens proteins.

Results are presented in FIGS. 20-23. FIG. 20 shows that the topical application of Aggrelyte-2A to mouse lenses did not reduce or otherwise change mouse lens transparency compared to vehicle-treated lenses. (In a separate study, Aggrelyte-2 and Aggrelyte-2C did not reduce or otherwise change human (60-62 years) lens transparency compared to vehicle-treated lenses. Data not shown.) FIGS. 21A and 21B show that the topical application of Aggrelyte-2A to mouse lenses reduced mouse lens stiffness by approximately 12% compared to vehicle-treated lenses for a 200-mg load. The reduction in stiffness was similar at 400- and 500-mg loads (FIGS. 21C and 21D, respectively). FIG. 22 shows that the topical application of Aggrelyte-2A to mouse lenses increased the density of AcK-bearing proteins in mouse lenses by approximately 10% compared to vehicle-treated lenses (*=$p<0.05$; **=$p<0.01$). FIG. 23 shows that the topical application of Aggrelyte-2A to mouse lenses increased the protein thiol content, via reduction of disulfide bonds, in mouse lenses by approximately 8% compared to vehicle-treated lenses. Collectively, the results demonstrate that aggrelytes may be safe and effective compounds for treating presbyopia by decreasing lens stiffness, solubilizing aggregated lens proteins, acetylating lens proteins, and/or reducing disulfide bonds to free thiol groups.

Example 21: Safety of Aggrelyte-2A as Evaluated by Anterior Segment-Optical Coherence Tomography Mice (four control and three aggrelyte-treated) were anesthetized with isoflurane. An Aggrelyte-2A and a Vehicle control formulation were prepared and applied as in Example 20. Phenylephrine (2%) and tropicamide (0.2%) drops were applied to the eye to dilate the pupil. Corneal cross-sectional scans (A-Scan/B-scan: 1000 lines, B-scan: 100 scans, Frames/B-scan: 4 frames) were obtained using an anterior segment-optical coherence tomography (AS-OCT) (Bioptigen, Durham, NC, USA), and the corneal epithelial thickness was measured using Bioptigen software.

Figure 24B:
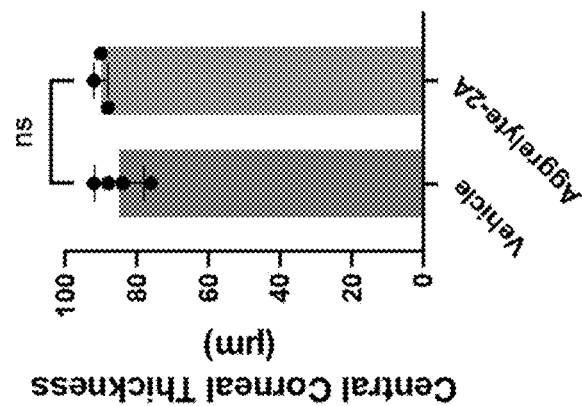
FIGS. 24A and 24B show the effects of topically applied Aggrelyte-2A on mouse lens corneas.
Figure 24A:
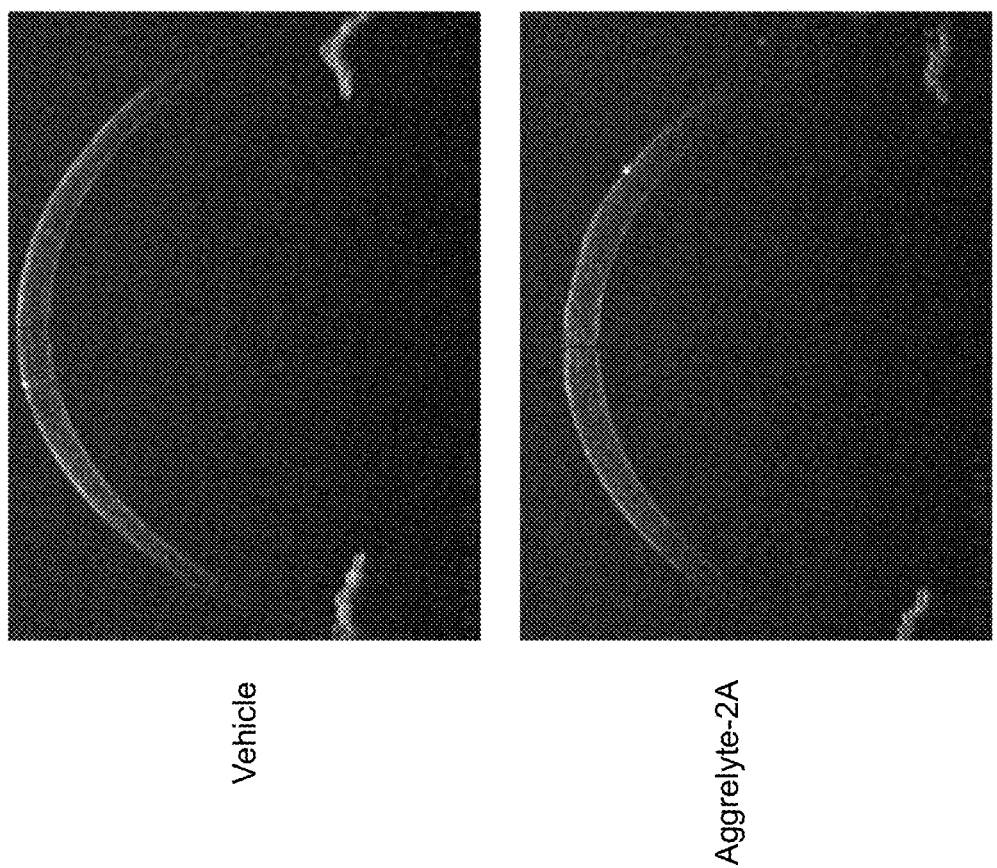

Results are presented in FIGS. 24A and 24B. Neither the vehicle-treated cornea, nor the cornea treated with Aggrelyte-2A, showed corneal edema (FIG. 24A). The central corneal thickness did not change after Aggrelyte-2A treatment. The results demonstrate that Aggrelyte-2A is safe for use on mouse corneas.

Example 22: Effects of Aggrelyte-2 and Aggrelyte-2A on the Stiffness of Ex Vivo Human Lenses To test the effects of Aggrelyte-2 and Aggrelyte-2A on human lenses (age: 47-67 years), lenses were incubated in media containing freshly dissolved aggrelyte (250 μM) for 48 hours, with aggrelyte replacement after 24 hours. One lens from each donor pair was treated with aggrelyte, while the other was used as the control. After incubation, lens stiffness was measured, as described above in Example 20.

Results are presented in FIGS. 25A-F. The results show that treating human lenses ex vivo with Aggrelyte-2A reduced human lens stiffness by approximately 15% compared to vehicle-treated lenses. For a 2000-mg load, the reduction was significant (*=$p<0.05$). The application of Aggrelyte-2 to human lenses ex vivo had no effect on stiffness. By comparison, Aggrelyte-2 reduced stiffness of mouse lenses comparably to Aggrelyte-2A when used at a lower concentration (250 uM instead of 1 mM) and for a shorter incubation time (48 hours instead of 72 hours) (see Example 18).

Example 23: Effects of Aggrelyte-2A on Levels of Acetylated Proteins in Human Lenses Each lens from Example 21 was decapsulated and homogenized in N2-bubbled 50 mM phosphate buffer, pH 7.4 (1.5 mL per lens), in a hand-held glass homogenizer. The sample was processed and evaluated for protein content as described in Example 19.

Figure 26:
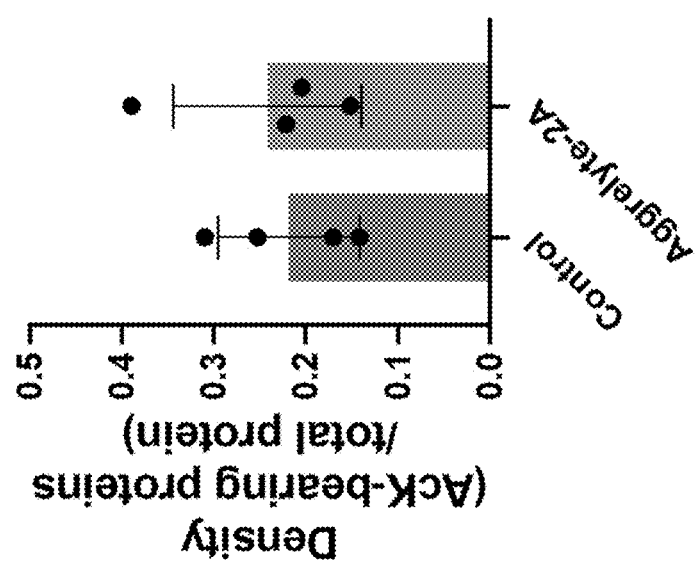
FIG. 26 is a bar graph showing the effects of Aggrelyte-2 on levels of acetylated proteins in human lenses.

The results are shown in FIG. 26. The results demonstrate that Aggrelyte-2A increased the density of acetyl-bearing proteins by approximately 5% compared to control lenses. The ability of an aggrelyte to acetylate lens proteins may help solubilize aggregated lens proteins and decrease lens stiffness.

Although various embodiments have been described above with a certain degree of particularity, or with reference to one or more individual embodiments, those skilled in the art could make numerous alterations to the disclosed embodiments without departing from the spirit or scope of this disclosure. Other embodiments are therefore contemplated. All matter contained in the above description and the accompanying drawings is illustrative only of particular embodiments and not limiting. Changes in detail, structure, or order of operation of steps of a method may be made without departing from the basic elements described herein.

The invention claimed is:

1. A method of treating, preventing, delaying, or reversing presbyopia in a human in need thereof, the method comprising administering to said human a therapeutically effective amount of a composition comprising an aggrelyte selected from the group consisting of N,S-diacetyl-L-cysteine methyl ester and S-acetyl-N-(3,3-dimethylbutanoyl)-L-cysteinate.

2. The method of claim 1, wherein the composition is administered topically.

3. The method of claim 1, wherein the composition is formulated as an ophthalmic drop, ophthalmic gel, or ophthalmic ointment.

4. The method of claim 1, wherein the composition is administered intracamerally, intravitreally, or intravenously.

5. The method of claim 1, wherein the composition is administered at least twice per day for four weeks.

6. A method of reducing eye lens stiffness in a human in need thereof, the method comprising administering to said human a therapeutically effective amount of a composition comprising an aggrelyte selected from the group consisting of N,S-diacetyl-L-cysteine methyl ester and S-acetyl-N-(3,3-dimethylbutanoyl)-L-cysteinate.

7. The method of claim 6, wherein axial strain in the eye lens is reduced.

8. The method of claim 6, wherein aggregated proteins in the eye lens are solubilized.

9. The method of claim 8, wherein at least a portion of the solubilized proteins are acetylated by the aggrelyte.

10. The method of claim 6, wherein the human is at least 40 years old.

11. A method of acetylating lysine residues in lens proteins in a human in need thereof, the method comprising administering to said human a therapeutically effective amount of a composition comprising an aggrelyte selected from the group consisting of N,S-diacetyl-L-cysteine methyl ester and S-acetyl-N-(3,3-dimethylbutanoyl)-L-cysteinate.

12. The method of claim 11, further comprising breaking disulfide bonds of the lens proteins.

13. The method of claim 11, wherein the lens proteins include crystallins.

14. The method of claim 13, wherein the crystallin includes at least one of α-crystallin and βB2-crystallin.

* * * * *